US008188315B2

(12) United States Patent
Hwang et al.

(10) Patent No.: US 8,188,315 B2
(45) Date of Patent: May 29, 2012

(54) ORGANIC LIGHT EMITTING DEVICE AND FLAT PANEL DISPLAY DEVICE COMPRISING THE SAME

(75) Inventors: Seok-Hwan Hwang, Suwon-si (KR); Young-Kook Kim, Suwon-si (KR); Yoon-Hyun Kwak, Suwon-si (KR); Jong-Hyuk Lee, Suwon-si (KR); Kwan-Hee Lee, Suwon-si (KR); Min-Seung Chun, Suwon-si (KR)

(73) Assignee: Samsung Mobile Display Co., Ltd., Giheung-Gu, Yongin, Gyunggi-Do (KR)

( * ) Notice: Subject to any disclaimer, the term of this patent is extended or adjusted under 35 U.S.C. 154(b) by 673 days.

(21) Appl. No.: 11/806,039

(22) Filed: May 29, 2007

(65) Prior Publication Data

US 2007/0231503 A1 Oct. 4, 2007

Related U.S. Application Data

(63) Continuation-in-part of application No. 11/286,421, filed on Nov. 25, 2005, now Pat. No. 8,021,764, and a continuation-in-part of application No. 11/181,706, filed on Jul. 13, 2005, now Pat. No. 7,431,997, and a continuation-in-part of application No. 11/097,182, filed on Apr. 4, 2005, now Pat. No. 7,737,627.

(30) Foreign Application Priority Data

| Apr. 2, 2004 | (KR) | 10-2004-0022877 |
| Jul. 14, 2004 | (KR) | 10-2004-0054700 |
| Nov. 29, 2004 | (KR) | 10-2004-0098747 |
| May 29, 2006 | (KR) | 10-2006-0048306 |

(51) Int. Cl.
C07D 209/82 (2006.01)
H01L 51/54 (2006.01)
C09K 11/06 (2006.01)

(52) U.S. Cl. ........ 564/440; 428/690; 428/917; 548/442; 564/427; 564/434

(58) Field of Classification Search .................. None
See application file for complete search history.

(56) References Cited

U.S. PATENT DOCUMENTS

| 4,356,429 A | 10/1982 | Tang |
| 6,008,588 A * | 12/1999 | Fujii ........................ 315/169.3 |
| 6,124,024 A | 9/2000 | Hosokawa et al. |
| 6,465,115 B2 | 10/2002 | Shi et al. |
| 6,485,847 B1 | 11/2002 | Uchida et al. |
| 6,517,957 B1 | 2/2003 | Senoo et al. |
| 6,596,415 B2 | 7/2003 | Shi et al. |
| 7,431,997 B2 * | 10/2008 | Hwang et al. ................. 428/690 |
| 2001/0010374 A1 * | 8/2001 | Takayama ........................ 257/98 |
| 2003/0076032 A1 | 4/2003 | Suzuri et al. |
| 2003/0224207 A1 | 12/2003 | Song et al. |
| 2004/0140757 A1 * | 7/2004 | Tyan et al. ..................... 313/504 |
| 2005/0062406 A1 | 3/2005 | Kinoshita |
| 2005/0067951 A1 | 3/2005 | Richter et al. |
| 2005/0162074 A1 | 7/2005 | Madathil et al. |
| 2005/0221124 A1 | 10/2005 | Hwang et al. |
| 2006/0017377 A1 | 1/2006 | Ryu |
| 2006/0020136 A1 | 1/2006 | Hwang et al. |
| 2006/0115680 A1 * | 6/2006 | Hwang et al. ................. 428/690 |
| 2006/0251924 A1 | 11/2006 | Lu et al. |
| 2007/0018569 A1 | 1/2007 | Kawamura et al. |
| 2007/0134512 A1 | 6/2007 | Klubek et al. |
| 2008/0107919 A1 | 5/2008 | Hwang et al. |
| 2009/0200928 A1 | 8/2009 | Hwang et al. |

FOREIGN PATENT DOCUMENTS

| EP | 1 661 888 A1 | 5/2006 |
| JP | 62280850 | 12/1987 |
| JP | 07150138 | 6/1995 |
| JP | 07234415 | 9/1995 |
| JP | 08003547 | 1/1996 |
| JP | 09013025 | 1/1997 |
| JP | 09268284 | 10/1997 |
| JP | 10168443 | 6/1998 |
| JP | 11144875 A * | 5/1999 |
| JP | 11329734 | 11/1999 |
| JP | 11329737 | 11/1999 |
| JP | 2002-252089 | 9/2002 |
| JP | 2003073343 | 3/2003 |
| JP | 2004-087393 | 3/2004 |
| JP | 2004-087395 | 3/2004 |

(Continued)

OTHER PUBLICATIONS

Machine translation of JP11-144875. Date of publication: May 28, 1999.*
Thomas et al. J. Am. Chem. Soc. 2001, 123, 9404-9411. Date of publication: Aug. 28, 2001.*
Korean Office Action issued by the Korean Patent Office on Nov. 27, 2007, corresponding to Korean Patent Application No. 2006-0048306.
The Extended European Search Report from the European Patent Office issued in Applicant's corresponding European Patent Application No. 07109066.6-2111 dated Nov. 7, 2007.

(Continued)

*Primary Examiner* — Lynda Salvatore
*Assistant Examiner* — Andrew K Bohaty
(74) *Attorney, Agent, or Firm* — Robert E. Bushnell, Esq.

(57) ABSTRACT

Provided are an organic light emitting device including: a substrate; a first electrode; a second electrode; and an organic layer interposed between the first electrode and the second electrode and including an emission layer, wherein one of the first electrode and the second electrode is a reflective electrode and the other is a semitransparent or transparent electrode, and wherein the organic layer includes a layer having at least one of the compounds having at least one carbazole group, and a flat panel display device including the organic light emitting device. The organic light emitting device has low driving voltage, excellent current density, high brightness, excellent color purity, high efficiency, and long lifetime.

3 Claims, 4 Drawing Sheets

FOREIGN PATENT DOCUMENTS

| | | |
|---|---|---|
| JP | 2004087371 | 3/2004 |
| JP | 2005097460 | 4/2005 |
| JP | 2005-290000 | 10/2005 |
| JP | 2005-294504 | 10/2005 |
| JP | 2005289914 | 10/2005 |
| JP | 2006-28176 | 2/2006 |
| JP | 2006-41471 | 2/2006 |
| JP | 2006-151979 | 6/2006 |
| JP | 2007-36188 | 2/2007 |
| JP | 2007055996 | 3/2007 |
| KR | 1020050078472 | 8/2005 |
| WO | WO 03/008515 | 1/2003 |
| WO | WO 2006/033492 A1 | 3/2006 |
| WO | 2007043484 | 4/2007 |

OTHER PUBLICATIONS

*The Partial European Search Report* from the European Patent Office issued in Applicant's corresponding European Patent Application No. 07109066.6-2111 dated Jul. 24, 2007.

Office action from Japanese Patent Office issued in Applicant's corresponding Japanese Patent Application No. 2007-110746 dated Jun. 1, 2010, and Request for Entry of the Accompanying Office Action for Japanese Office action attached herewith.

Thomas et al., Green and Yellow Electroluminescent Dipolar Carbazole Derivatives: Features and Benefits of Electron-Withdrawing Segments, Chem. Mater. (2002) 14, pp. 3852-3859. Cited by Applicants in parent application U.S. Appl. No. 11/097,182.

Shen et al., High Tg blue emitting materials for electroluminescent devices, J. Mater. Chem. (2005) 15, pp. 2455-2463. In parent application U.S. Appl. No. 11/097,182.

Adachi et al., Endothermic energy transfer: A mechanism for generating very efficient high-energy phosphorescent emission in organic materials, Appl. Phys. Lett. (2001) 79, 13, pp. 2082-2084. Cited by Applicants in parent application U.S. Appl. No. 11/286,421.

Kuwabara et al., Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials, Adv. Mater. (1994) 6, 9, pp. 677-679. Cited by Applicants in parent application U.S. Appl. No. 11/286,421.

\* cited by examiner

ORGANIC LIGHT EMITTING DEVICE AND FLAT PANEL DISPLAY DEVICE COMPRISING THE SAME

CROSS-REFERENCE TO RELATED PATENT APPLICATION

This application is a Continuation-in-Part of the following Applicants Patent Applications: 1) Ser. No. 11/286,421 filed in the U.S. Patent & Trademark Office on the 25 of Nov. 2005; now U.S. Pat. No. 8,021,764 2) Ser. No. 11/181,706 filed in the U.S. Patent & Trademark Office on the 13 of Jul. 2005; now U.S. Pat. No. 7,431,997 and 3) Ser. No. 11/097,182 filed in the U.S. Patent & Trademark Office on the 4 of Apr. 2005, now U.S. Pat. No. 7,737,627 and assigned to the assignee of the present invention. All benefits accruing under 35 U.S.C. §120 from the parent application are also hereby claimed.

CLAIM OF PRIORITY

This application claims the benefit of the following Korean Patent Applications: 1) No. 10-2006-0048306, filed on May 29, 2006; 2) No. 10-2004-0098747, filed on 29 Nov. 2004; 3) No. 10-2004 -0054700, filed on 14 Jul. 2004; and 4) No. 10-2004-0022877, filed on 2 Apr. 2004 in the Korean Intellectual Property Office, the disclosure of which is incorporated herein in its entirety by reference.

BACKGROUND OF THE INVENTION

1. Field of the Invention

The present invention relates to an organic light emitting device and a flat panel display device, and more particularly, to an organic light emitting device including an organic layer containing a phenylcarbazole-based compound.

2. Description of the Related Art

Organic light emitting devices are self-emission displays that emit light by recombination of electrons and holes in an organic layer made of a fluorescent or phosphorescent compound when a current is applied to the organic layer. Organic light emitting devices are lightweight, have simple constituent elements, an easy fabrication process, superior image quality, and a wide viewing angle. Furthermore, organic light emitting devices can realize dynamic images and high color purity. Organic light emitting devices also have electrical properties such as low power consumption and low driving voltage suitable for portable electronic equipment.

Organic light emitting devices generally have an organic layer in the form of a multi-layer structure including an electron injection layer, an emission layer, a hole transport layer, etc. instead of including only a single emission layer to improve efficiency and to lower driving voltage. For example, Japanese Patent Laid-Open Publication No. 2002-252089 discloses an organic light emitting device including a hole transport layer.

However, the driving voltage, current density, brightness, color purity, efficiency and lifetime of a conventional organic light emitting device do not meet desired levels. Accordingly, these properties must be improved.

SUMMARY OF THE INVENTION

The present invention provides an improved organic light emitting device.

The present invention provides an organic light emitting device including an organic layer containing a compound that has excellent hole mobility between a pair of electrodes capable of generating resonance during the operation of the light emitting device, an organic light emitting device including a hole injection layer having a predetermined range of thickness between a pair of electrodes capable of generating resonance during the operation of the light emitting device, and a flat panel display device including the organic light emitting device.

According to an aspect of the present invention, there is provided an organic light emitting device including: a substrate; a first electrode; a second electrode; and an organic layer interposed between the first electrode and the second electrode and including an emission layer, wherein one of the first electrode and the second electrode is a reflective electrode and the other is a semitransparent or transparent electrode, and wherein the organic layer comprises a layer including at least one of compounds represented by Formulae 1, 2, and 3 below.

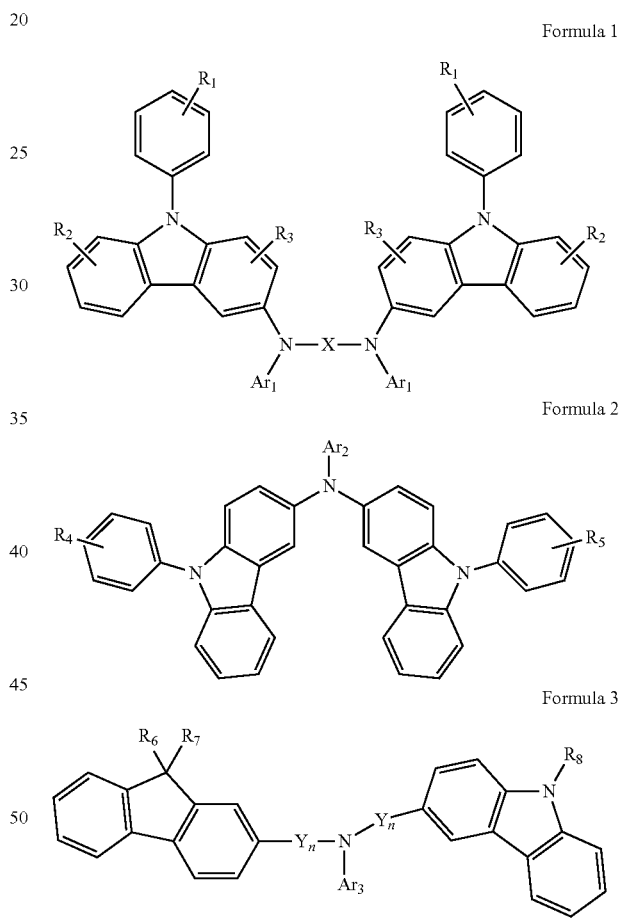

Formula 1

Formula 2

Formula 3

Here, X is one of a substituted or unsubstituted $C_1$-$C_{30}$ alkylene group, a substituted or unsubstituted $C_2$-$C_{30}$ alkenylene group, a substituted or unsubstituted $C_6$-$C_{30}$ arylene group, a substituted or unsubstituted $C_2$-$C_{30}$ heteroarylene group, and a substituted or unsubstituted $C_2$-$C_{30}$ hetero ring;

Each $R_1$, each $R_2$, each $R_3$, $R_4$, $R_5$, $R_6$, $R_7$ and $R_8$ are each independently one of a hydrogen atom, a substituted or unsubstituted $C_1$-$C_{30}$ alkyl group, a substituted or unsubstituted $C_1$-$C_{30}$ alkoxy group, a substituted or unsubstituted $C_6$-$C_{30}$ aryl group, a substituted or unsubstituted $C_6$-$C_{30}$ aryloxy group, a substituted or unsubstituted $C_2$-$C_{30}$ hetero ring, a substituted or unsubstituted $C_5$-$C_{30}$ polycyclic condensed ring, a hydroxy group, a cyano group, and a substituted or unsubstituted amino group, wherein two or more of $R_1$, $R_2$ and $R_3$ can be optionally bound with one another to form a saturated or unsaturated carbon ring, $R_4$ and $R_5$, can be optionally bound with one another to form a saturated or unsaturated carbon ring, and two or more of $R_6$, $R_7$ and $R_8$ can be optionally bound with one another to form a saturated or unsaturated carbon ring;

each $Ar_1$, $Ar_2$ and $Ar_3$ are each independently a substituted or unsubstituted $C_6$-$C_{30}$ aryl group or a substituted or unsubstituted $C_2$-$C_{30}$ heteroaryl group;

each Y is independently one of a substituted or unsubstituted $C_1$-$C_{30}$ alkyl group, a substituted or unsubstituted $C_6$-$C_{30}$ aryl group, and a substituted or unsubstituted $C_2$-$C_{30}$ hetero ring; and each n is independently an integer from 0 to 5.

According to another aspect of the present invention, there is provided an organic light emitting device including: a substrate; a first electrode; a second electrode; and an organic layer interposed between the first electrode and the second electrode and including an emission layer having a red emission region and a hole injection layer having a region formed under the red emission region, wherein one of the first electrode and the second electrode is a reflective electrode and the other is a semitransparent or transparent electrode, and wherein the thickness of the region of the hole injection layer formed under the red emission region is in the range of 1,600 to 2,200 Å.

According to another aspect of the present invention, there is provided an organic light emitting device including: a substrate; a first electrode; a second electrode; and an organic layer interposed between the first electrode and the second electrode and including an emission layer having a green emission region and a hole injection layer having a region formed under the green emission region, wherein one of the first electrode and the second electrode is a reflective electrode and the other is a semitransparent or transparent electrode, and wherein the thickness of the region of the hole injection layer formed under the green emission region is in the range of 1,400 to 1,800 Å.

According to another aspect of the present invention, there is provided an organic light emitting device including: a substrate; a first electrode; a second electrode; and an organic layer interposed between the first electrode and the second electrode and including an emission layer having a blue emission region and a hole injection layer having a region formed under the blue emission region, wherein one of the first electrode and the second electrode is a reflective electrode and the other is a semitransparent or transparent electrode, and wherein the thickness of the region of the hole injection layer formed under the blue emission region is in the range of 1,000 to 1,400 Å.

According to another aspect of the present invention, there is provided a flat panel display device including the organic light emitting device, wherein the first electrode of the organic light emitting device is electrically connected to a source electrode or a drain electrode of a thin film transistor.

The organic light emitting device has low driving voltage, excellent current density, high brightness, excellent color purity, high efficiency, and long lifetime. Particularly, the organic light emitting device has excellent lifetime.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1:
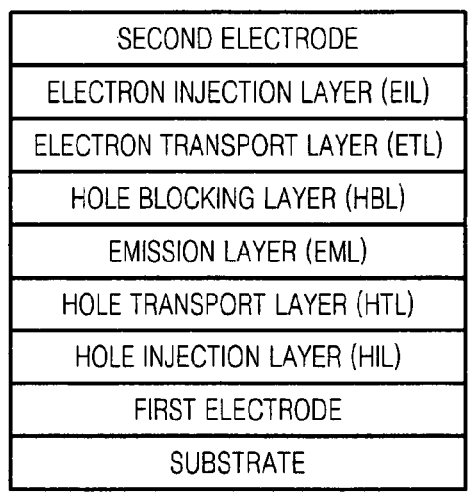
FIG. 1 schematically illustrates a structure of an organic light emitting device according to an embodiment of the present invention.

Hereinafter, the present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art.

An organic light emitting device according to an embodiment of the present invention includes a substrate, a first electrode, a second electrode and an organic layer. The organic layer is disposed between the first electrode and the second electrode and includes an emission layer. The organic layer can emit red, green, and/or blue light according to a material used to form the emission layer.

One of the first electrode and the second electrode is a reflective electrode and the other is a semitransparent or transparent electrode. Accordingly, resonance may occur between the first electrode and the second electrode during the operation of the light emitting device. Thus, the light generated in the organic layer between the first electrode and the second electrode resonates between the first electrode and the second electrode during the operation of the light emitting device, and the light is extracted from of the organic light emitting device. Thus, luminance of the light and light emitting efficiency can be enhanced.

The first electrode may be formed on the substrate. For example, the first electrode may be a reflective electrode, and the second electrode may be a semitransparent or transparent electrode. Accordingly, the light generated in the organic layer between the first electrode and the second electrode resonates between the first electrode and the second electrode during the operation of the light emitting device, and the light is extracted through the second electrode, that is, in a direction away from the substrate.

The organic layer of the organic light emitting device according to the current embodiment of the present invention may include a layer containing a phenylcarbazole-based compound. In particular, the organic layer may include a layer including at least one of the compounds represented by Formulae 1, 2, and 3 below.

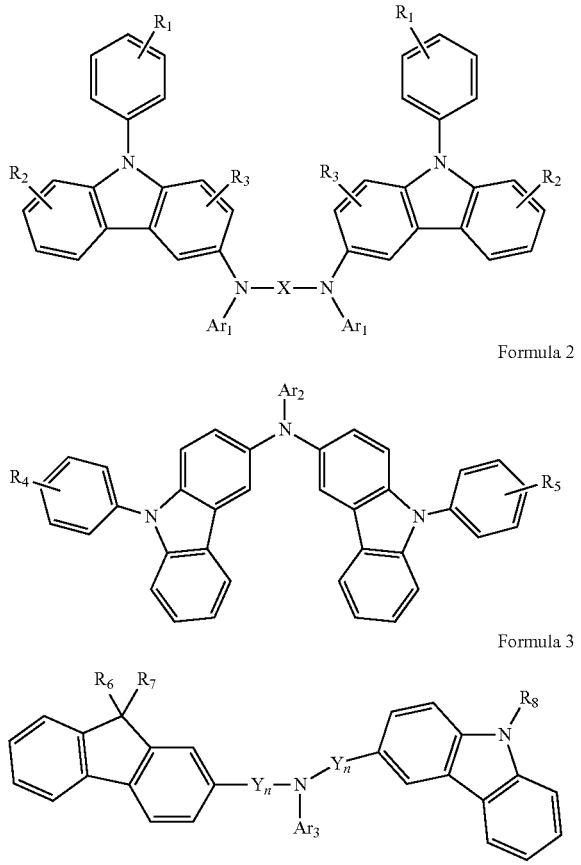

Formula 1

Formula 2

Formula 3

Here, X is one of a substituted or unsubstituted $C_1$-$C_{30}$ alkylene group, a substituted or unsubstituted $C_2$-$C_{30}$ alkenylene group, a substituted or unsubstituted $C_6$-$C_{30}$ arylene group, a substituted or unsubstituted $C_2$-$C_{30}$ heteroarylene group, and a substituted or unsubstituted $C_2$-$C_{30}$ hetero ring;

Each $R_1$, each $R_2$, each $R_3$, $R_4$, $R_5$, $R_6$, $R_7$ and $R_8$ are each independently one of a hydrogen atom, a substituted or unsubstituted $C_1$-$C_{30}$ alkyl group, a substituted or unsubstituted $C_1$-$C_{30}$ alkoxy group, a substituted or unsubstituted $C_6$-$C_{30}$ aryl group, a substituted or unsubstituted $C_6$-$C_{30}$ aryloxy group, a substituted or unsubstituted $C_2$-$C_{30}$ hetero ring, a substituted or unsubstituted $C_5$-$C_{30}$ polycyclic condensed ring, a hydroxy group, a cyano group, and a substituted or unsubstituted amino group, wherein two or more of $R_1$, $R_2$ and $R_3$ can be optionally bound with one another to form a saturated or unsaturated carbon ring, $R_4$ and $R_5$, can be optionally bound with one another to form a saturated or unsaturated carbon ring, and two or more of $R_6$, $R_7$ and $R_8$ can be optionally bound with one another to form a saturated or unsaturated carbon ring;

each $Ar_1$, $Ar_2$ and $Ar_3$ are each independently a substituted or unsubstituted $C_6$-$C_{30}$ aryl group or a substituted or unsubstituted $C_2$-$C_{30}$ heteroaryl group;

each Y is independently one of a substituted or unsubstituted $C_1$-$C_{30}$ alkyl group, a substituted or unsubstituted $C_6$-$C_{30}$ aryl group, and a substituted or unsubstituted $C_2$-$C_{30}$ hetero ring; and each n is independently an integer from 0 to 5.

The compounds represented by Formulae 1, 2, and 3 have a stiff carbazole group, and thus the glass transition temperature or the melting point of the compounds increases. During the operation of the organic light emitting device according to the current embodiment of the present invention, the compounds are highly resistant to heat generated in the organic layer, between the organic layers, or between the organic layer and the electrode according to Joule's Law, and are stable in a high temperature environment. Thus, when the compounds are used to form the organic layer of the organic light emitting device of the present embodiment, long lifetime and excellent luminance can be obtained.

In particular, the compounds represented by Formulae 1 and 2 which have two or more carbazole groups may provide long lifetime and excellent brightness.

In addition, the organic light emitting device of the present embodiment including an organic layer containing a compound represented by Formula 1, 2, or 3 has excellent stability during storage and operation. This feature can be explained by, for example, but not limited to, a high Tg (glass transition temperature) of the compound represented by Formula 1, 2, or 3.

The compound represented by Formula 1 may include a compound represented by Formula 1a below, but is not limited thereto.

Formula 1a

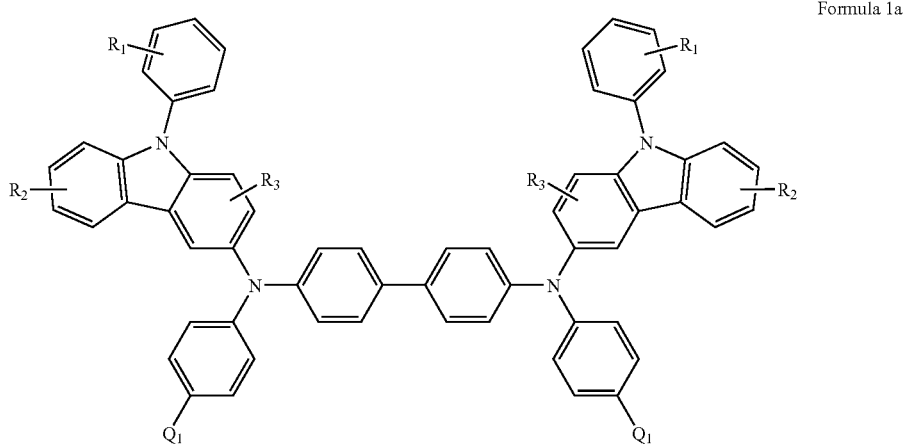

Here, each $R_1$, each $R_2$, and each $R_3$ are each independently one of a hydrogen atom, a substituted or unsubstituted $C_1$-$C_{30}$ alkyl group, a substituted or unsubstituted $C_1$-$C_{30}$ alkoxy group, a substituted or unsubstituted $C_6$-$C_{30}$ aryl group, a substituted or unsubstituted $C_6$-$C_{30}$ aryloxy group, a substituted or unsubstituted $C_2$-$C_{30}$ hetero ring, a substituted or unsubstituted $C_5$-$C_{30}$ polycyclic condensed ring, a hydroxy group, a cyano group, and a substituted or unsubstituted amino group, wherein two or more of $R_1$, $R_2$ and $R_3$ can be optionally bound with one another to form a saturated or unsaturated carbon ring; and each $Q_1$ is independently one of a hydrogen atom, a cyano group, a fluorine atom, a substituted or unsubstituted $C_1$-$C_{30}$ alkyl group, a substituted or unsubstituted $C_6$-$C_{30}$ aryl group, a substituted or unsubstituted $C_2$-$C_{30}$ hetero ring, and a substituted or unsubstituted amino group.

The compound represented by Formula 1 may include a compound represented by Formula 1b below, but is not limited thereto.

Here, $R_4$ and $R_5$ are each independently one of a hydrogen atom, a substituted or unsubstituted $C_1$-$C_{30}$ alkyl group, a substituted or unsubstituted $C_1$-$C_{30}$ alkoxy group, a substituted or unsubstituted $C_6$-$C_{30}$ aryl group, a substituted or unsubstituted $C_6$-$C_{30}$ aryloxy group, a substituted or unsubstituted $C_2$-$C_{30}$ hetero ring, a substituted or unsubstituted $C_5$-$C_{30}$ polycyclic condensed ring, a hydroxy group, a cyano group, and a substituted or unsubstituted amino group, wherein $R_4$, and $R_5$ can be optionally bound with one another to form a saturated or unsaturated carbon ring; and $Q_3$ is one of a hydrogen atom, a cyano group, a fluorine atom, a substituted or unsubstituted $C_1$-$C_{30}$ alkyl group, a Formula 1b

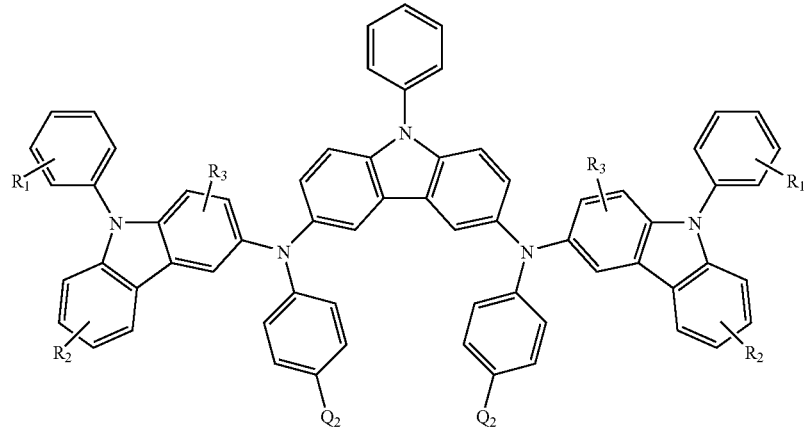

Here, each $R_1$, each $R_2$, and each $R_3$ are each independently one of a hydrogen atom, a substituted or unsubstituted $C_1$-$C_{30}$ alkyl group, a substituted or unsubstituted $C_1$-$C_{30}$ alkoxy group, a substituted or unsubstituted $C_6$-$C_{30}$ aryl group, a substituted or unsubstituted $C_6$-$C_{30}$ aryloxy group, a substituted or unsubstituted $C_2$-$C_{30}$ hetero ring, a substituted or unsubstituted $C_5$-$C_{30}$ polycyclic condensed ring, a hydroxy group, a cyano group, and a substituted or unsubstituted amino group, wherein two or more of $R_1$, $R_2$ and $R_3$ can be optionally bound with one another to form a saturated or unsaturated carbon ring; and each $Q_2$ is one selected from the group consisting of a hydrogen atom, a cyano group, a fluorine atom, a substituted or unsubstituted $C_1$-$C_{30}$ alkyl group, a substituted or unsubstituted $C_6$-$C_{30}$ aryl group, a substituted or unsubstituted $C_2$-$C_{30}$ hetero ring, and a substituted or unsubstituted amino group.

The compound represented by Formula 2 may include a compound represented by Formula 2a below, but is not limited thereto.

substituted or unsubstituted $C_6$-$C_{30}$ aryl group, a substituted or unsubstituted $C_2$-$C_{30}$ hetero ring, and a substituted or unsubstituted amino group.

The compound represented by Formula 3 may include a compound represented by Formula 3a below, but is not limited thereto.

Formula 3a

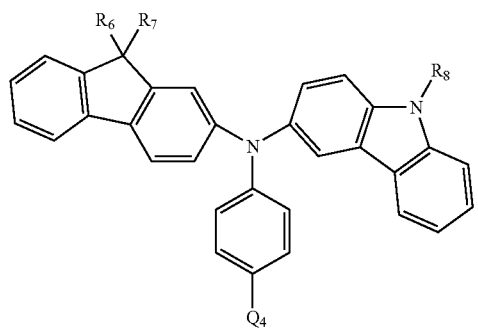

Here, $R_6$, $R_7$ and $R_8$ are each independently one of a hydrogen atom, a substituted or unsubstituted $C_1$-$C_{30}$ alkyl group, a substituted or unsubstituted $C_1$-$C_{30}$ alkoxy group, a substituted or unsubstituted $C_6$-$C_{30}$ aryl group, a substituted or unsubstituted $C_6$-$C_{30}$ aryloxy group, a substituted or unsubstituted $C_2$-$C_{30}$ hetero ring, a substituted or unsubstituted $C_5$-$C_{30}$ polycyclic condensed ring, a hydroxy group, a cyano group, and a substituted or unsubstituted amino group, wherein two or more of $R_6$, $R_7$ and $R_8$ can be optionally bound with one another to form a saturated or unsaturated carbon ring; and Formula 2a

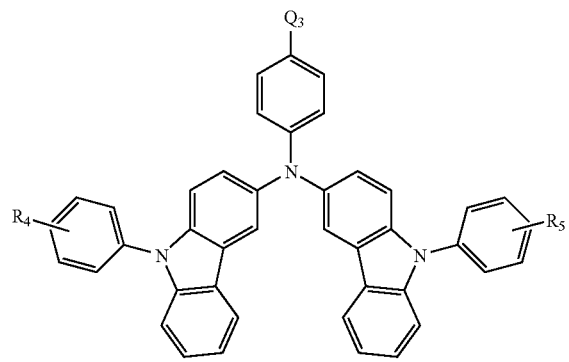

$Q_4$ is one of a hydrogen atom, a cyano group, a fluorine atom, a substituted or unsubstituted $C_1$-$C_{30}$ alkyl group, a substituted or unsubstituted $C_6$-$C_{30}$ aryl group, a substituted or unsubstituted $C_2$-$C_{30}$ hetero ring, and a substituted or unsubstituted amino group.

Hereinafter, examples of the groups used to form the compounds represented by the above formulae will now be described in more detail.

Examples of the unsubstituted $C_1$-$C_{30}$ alkyl group may include a methyl group, an ethyl group, a propyl group, an isobutyl group, a sec-butyl group, a pentyl group, an iso-amyl group, and a hexyl group. At least one hydrogen atom in the unsubstituted $C_1$-$C_{30}$ alkyl group may be substituted with a halogen atom, a $C_1$-$C_{30}$ alkyl group, a $C_1$-$C_{30}$ alkoxy group, a low alkylamino group, a hydroxy group, a nitro group, a cyano group, an amino group, an amidino group, a hydrazine group, a hydrazone group, a carboxyl group, a sulfonic acid group, and a phosphoric acid group.

Examples of the unsubstituted $C_1$-$C_{30}$ alkoxy group may include a methoxy group, an ethoxy group, a propoxy group, an isobutyloxy group, a sec-butyloxy group, a pentyloxy group, an iso-amyloxy group, and a hexyloxy group. At least one hydrogen atom in the unsubstituted $C_1$-$C_{30}$ alkoxy group may be substituted with the groups described above with reference to the $C_1$-$C_{30}$ alkyl group.

The $C_6$-$C_{30}$ aryl group indicates a carbocyclic aromatic system containing one or more rings, wherein such rings may be bonded together in a pendent manner or may be fused. The term "aryl group" may include an aromatic system such as a phenyl group, a naphthyl group, and a tetrahydronaphthyl group. At least one hydrogen atom in the $C_6$-$C_{30}$ aryl group may be substituted with the groups described above with reference to the $C_1$-$C_{30}$ alkyl group.

The $C_2$-$C_{30}$ heteroaryl group indicates a monovalent monocyclic ring compound having 2 to 30 membered rings including C and 1 to 3 hetero atoms selected from the group consisting of N, O, P, and S, wherein such rings may be bonded together in a pendent manner or may be fused. Examples of the $C_2$-$C_{30}$ heteroaryl group may include a pyridyl group, a thienyl group, and a furyl group. At least one hydrogen atom in the $C_2$-$C_{30}$ heteroaryl group may be substituted with the groups described above with reference to the $C_1$-$C_{30}$ alkyl group.

Each $Ar_1$, $Ar_2$ and $Ar_3$ are each independently a phenyl group, a $C_1$-$C_{10}$ alkylphenyl group, a $C_1$-$C_{10}$ alkoxyphenyl group, a halophenyl group, a cyanophenyl group, a dicyanophenyl group, a trifluoromethoxyphenyl group, an o-, m-, or p-tolyl group, an o-, m- or p-cumenyl group, a mesityl group, a phenoxyphenyl group, a ($\alpha,\alpha$-dimethylbenzene) phenyl group, a (N,N'-dimethyl)aminophenyl group, a (N,N'-diphenyl)aminophenyl group, a ($C_1$-$C_{10}$ alkylcyclohexyl) phenyl group, an (anthracenyl)phenyl group, a biphenyl group, a $C_1$-$C_{10}$ alkylbiphenyl group, a $C_1$-$C_{10}$ alkoxybiphenyl group, a pentalenyl group, an indenyl group, a naphthyl group, a $C_1$-$C_{10}$ alkylnaphthyl group, a $C_1$-$C_{10}$ alkoxynaphthyl group, a halonaphthyl group, a cyanonaphthyl group, a biphenylenyl group, a $C_1$-$C_{10}$ alkyl biphenylenyl group, a $C_1$-$C_{10}$ alkoxy biphenylenyl group, an anthracenyl group, an azulenyl group, a heptalenyl group, an acenaphthylenyl group, a phenalenyl group, a fluorenyl group, an anthraquinolyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, a $C_1$-$C_{10}$ alkyl carbazolyl group, a thiophenyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridinyl group, a pyridazinyl group, a pyrimidinyl group, a pyrazinyl group, and a thianthrenyl group, but are not limited thereto.

More particularly, the compounds represented by Formulae 1, 2, and 3 are each independently one of Compounds 1 to 62 below, but are not limited thereto.

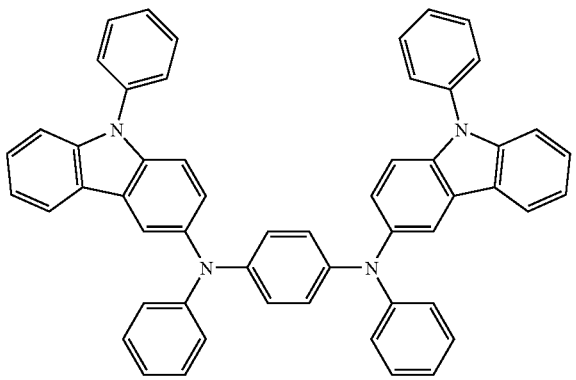

1

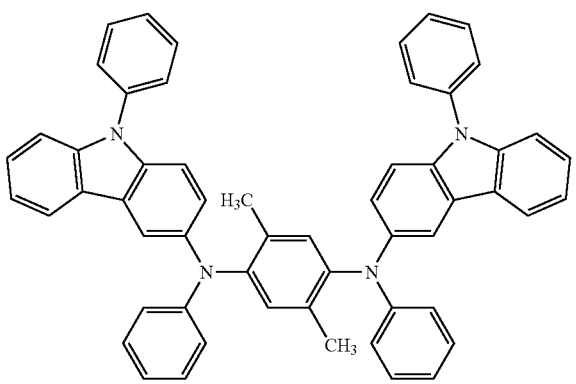

2

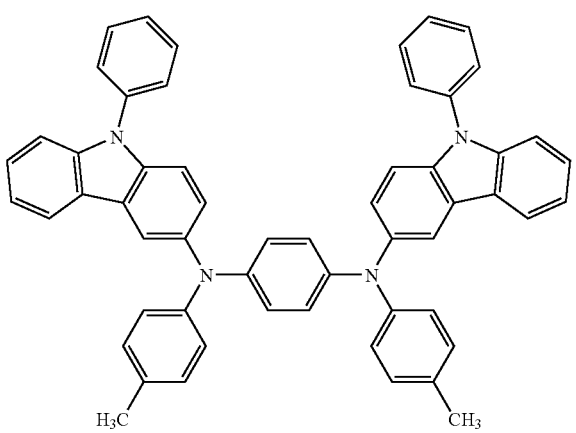

3

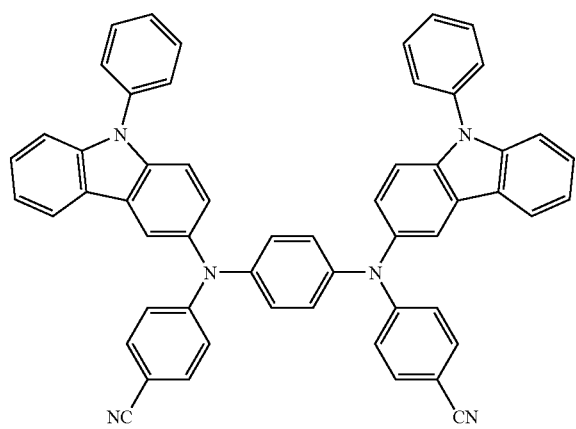
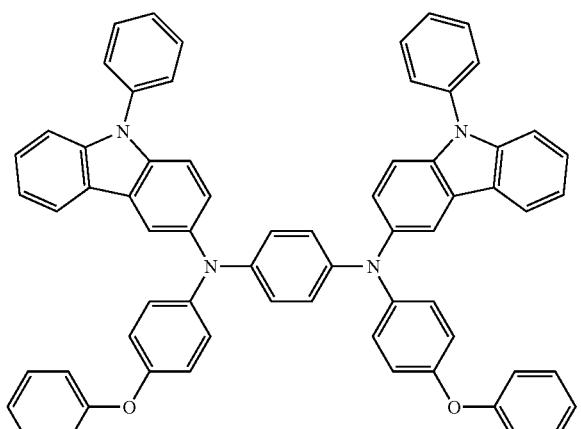
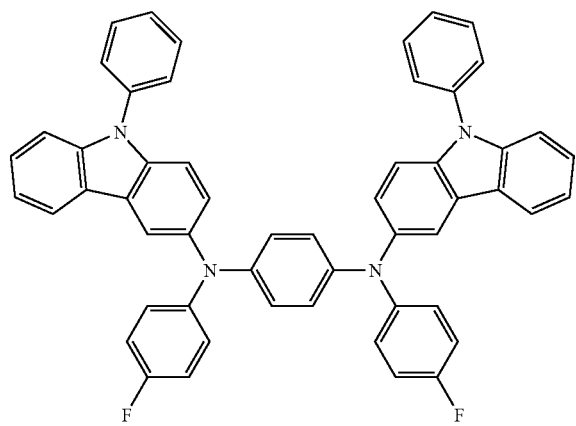
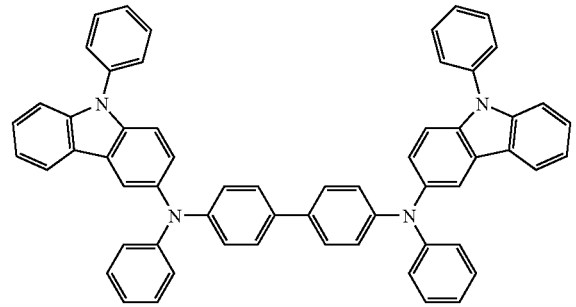
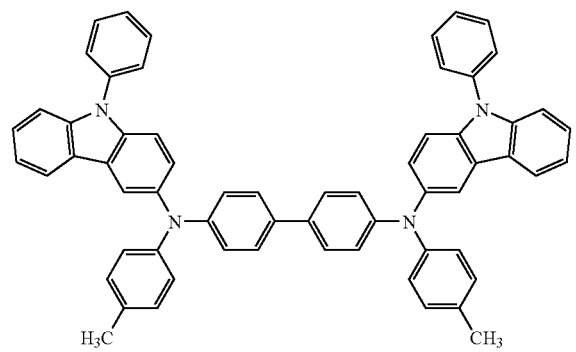
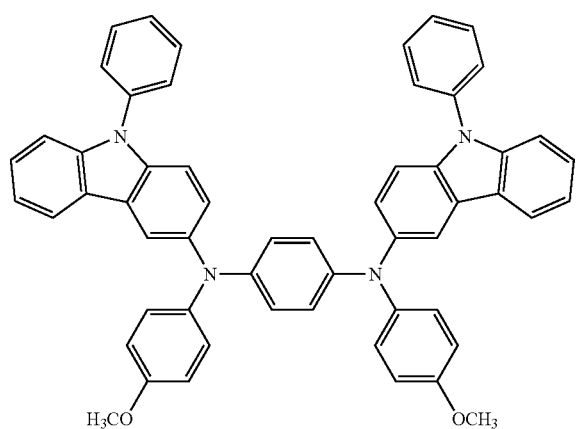
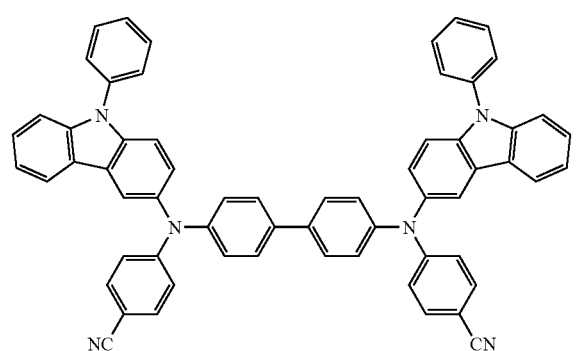

11
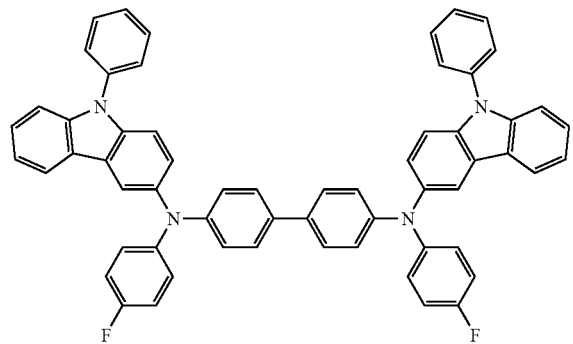
12
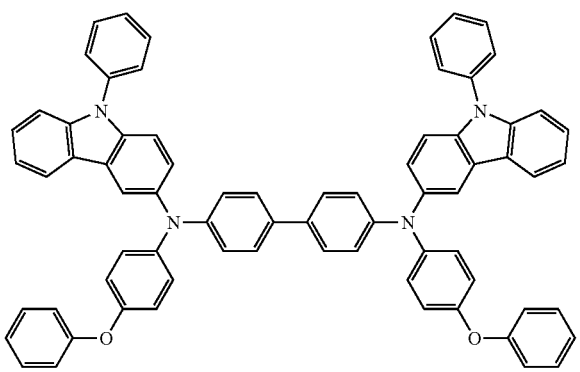
13
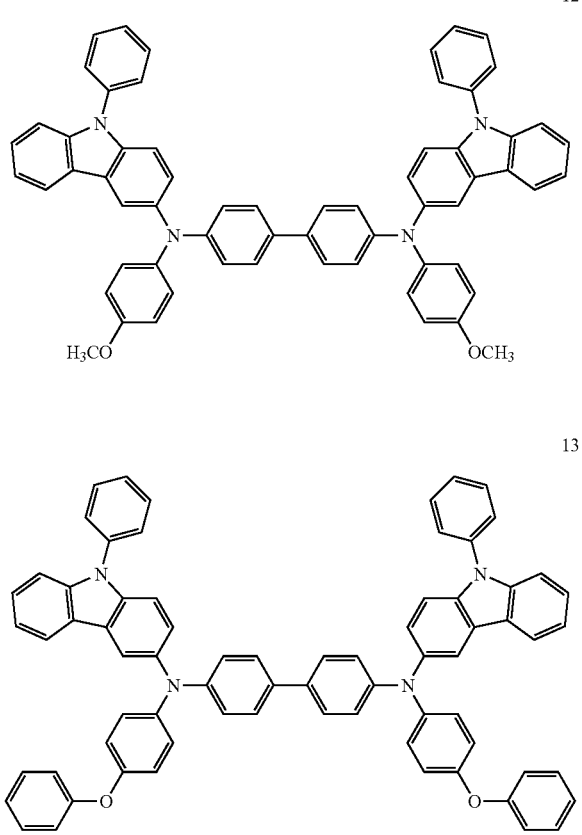
14
15
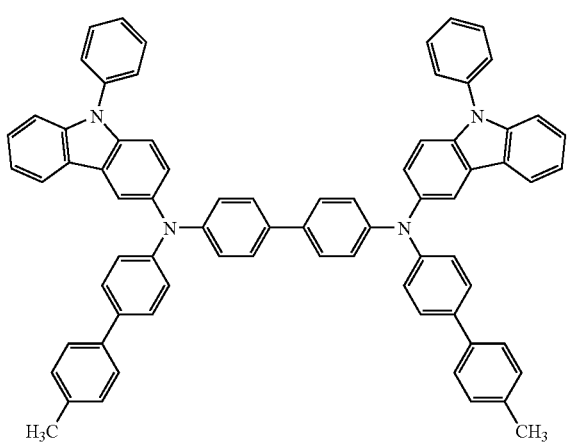
16
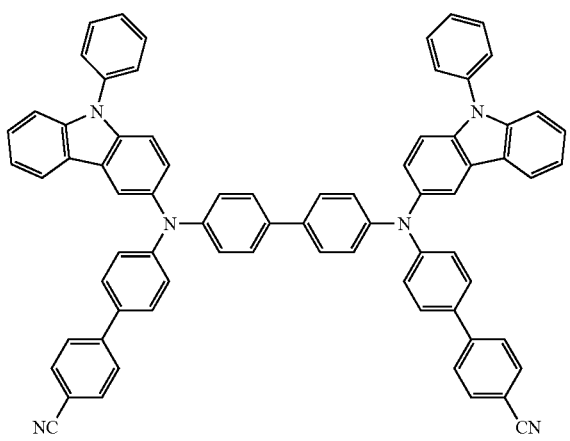
17
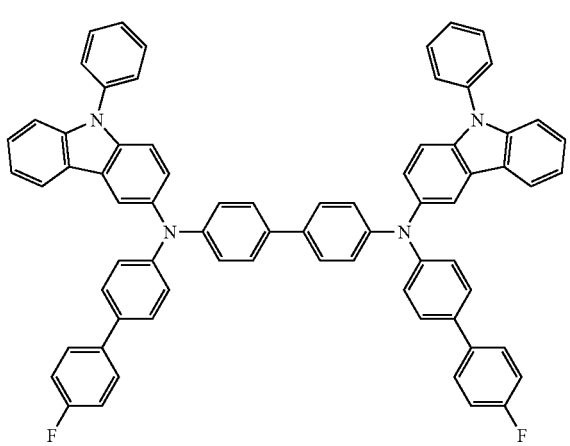

18
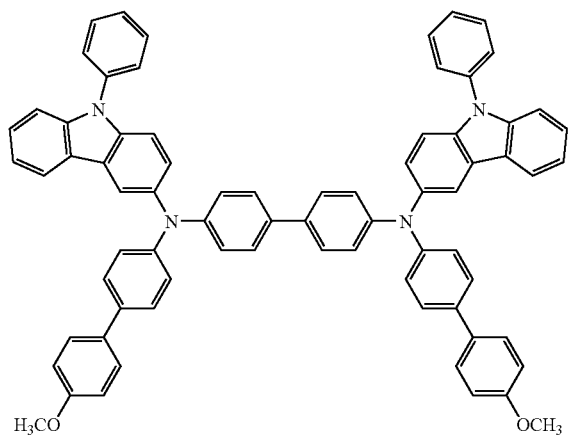
21
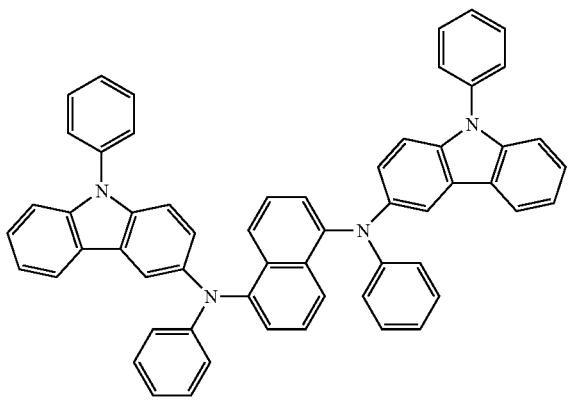
19
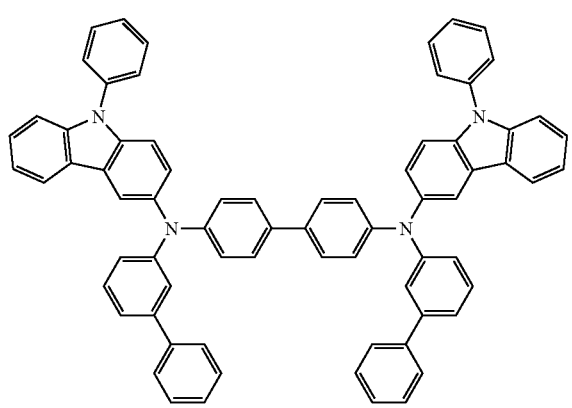
22
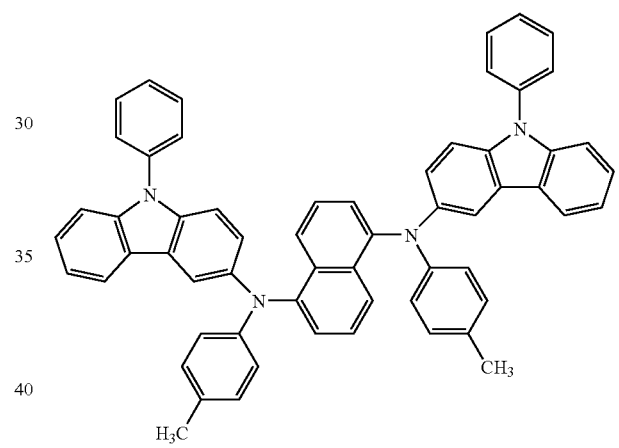
20
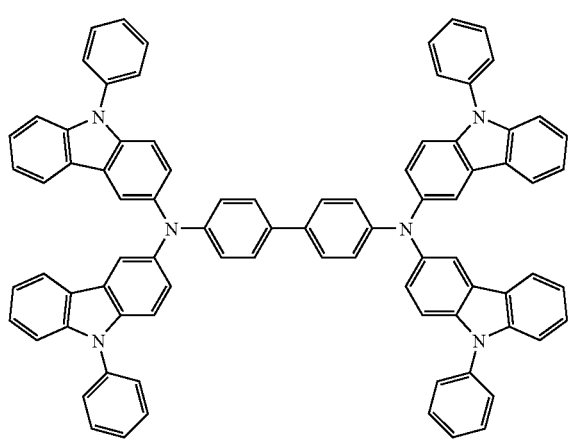
23
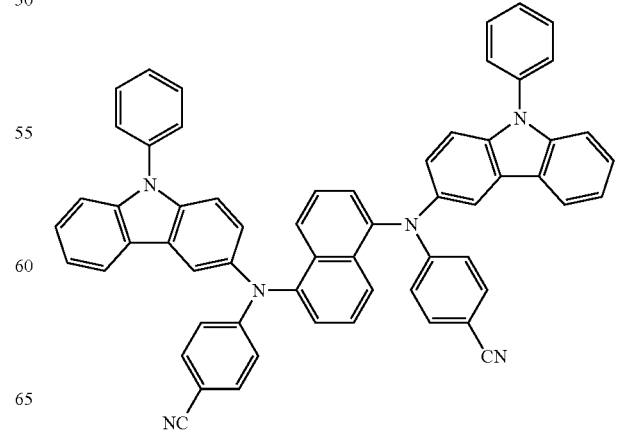

24
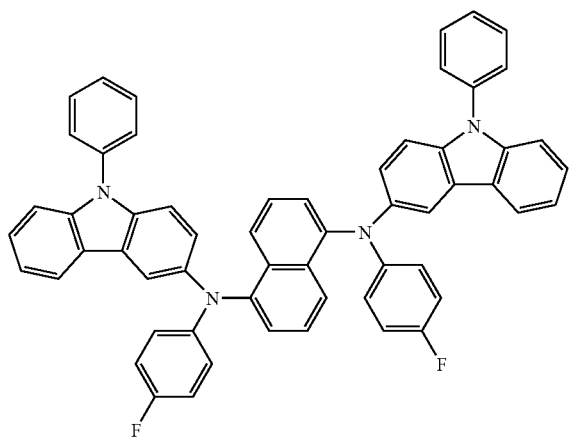
25
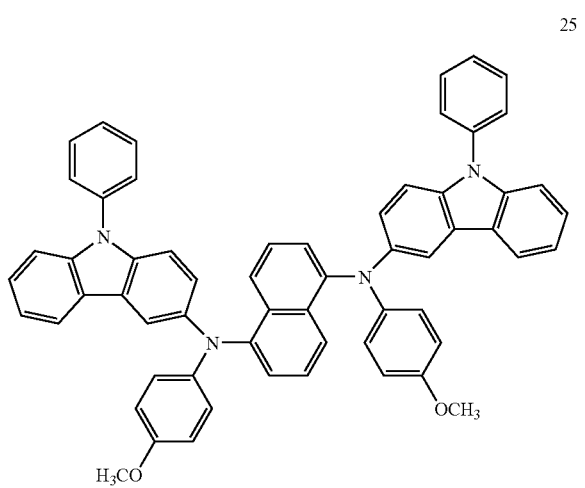
26
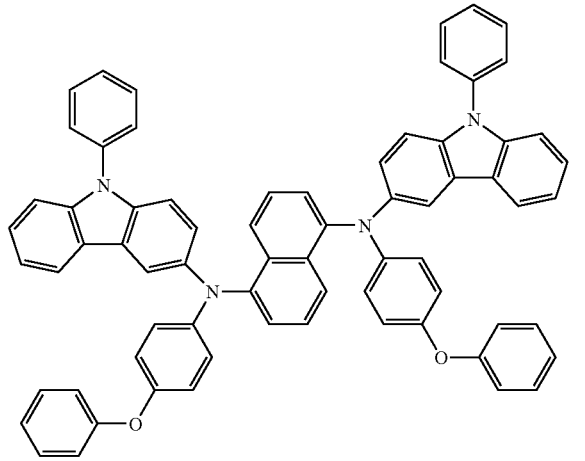
27
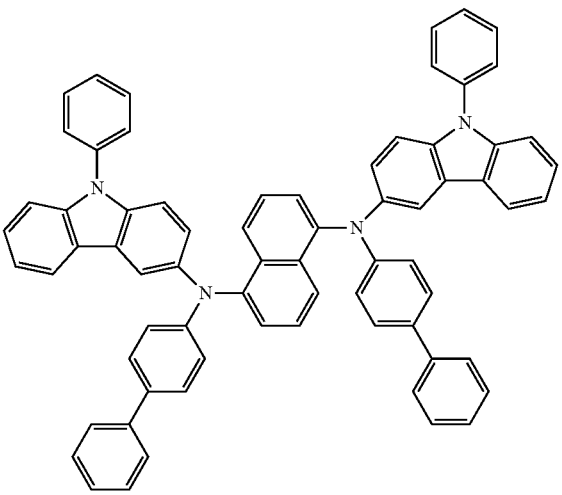
28
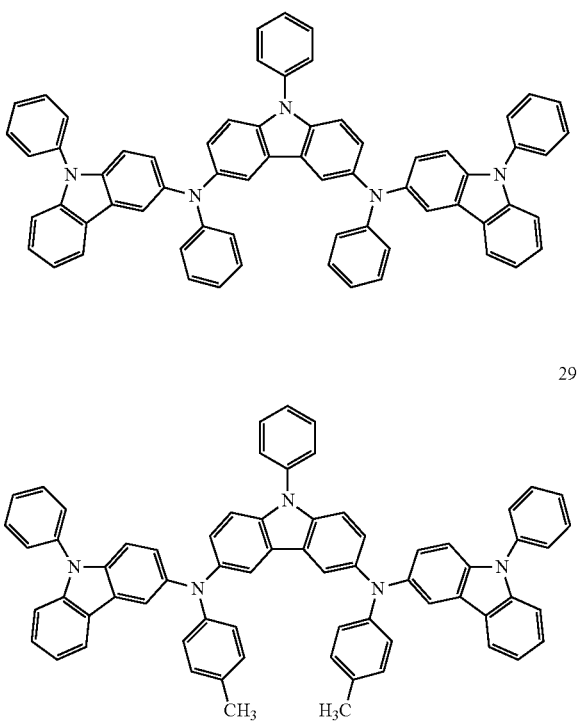
29
30
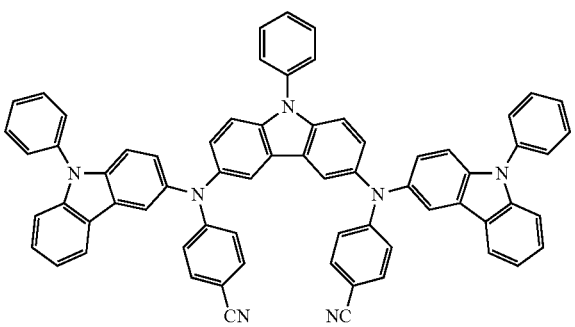

31
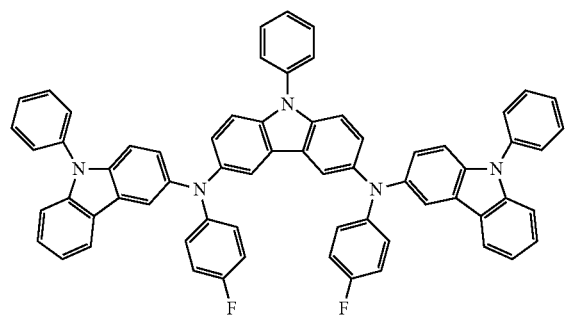
32
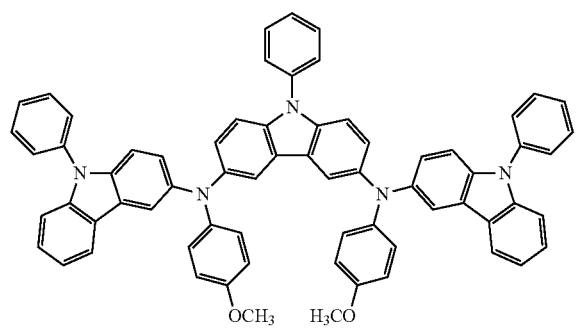
33
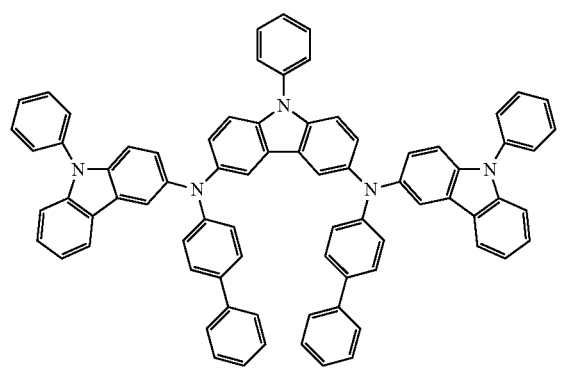
34
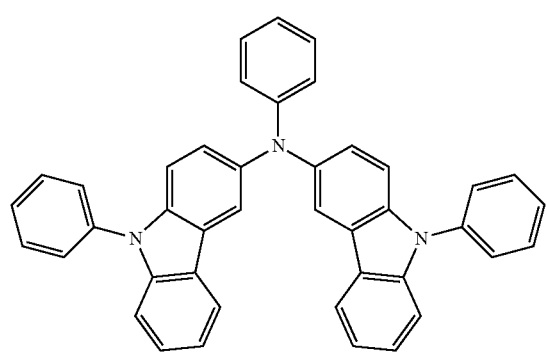
35
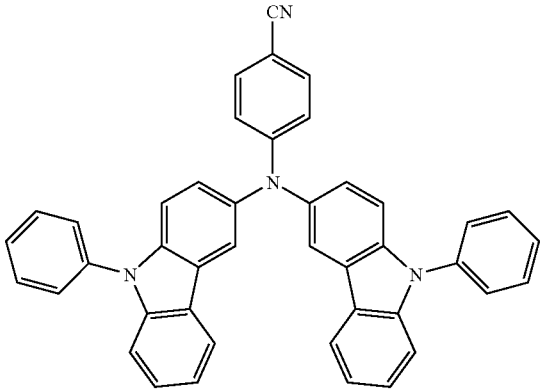
36
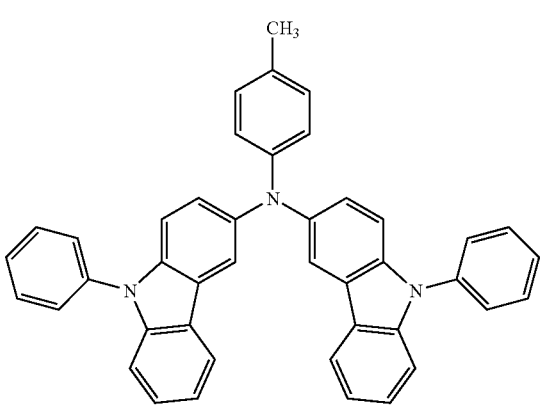
37
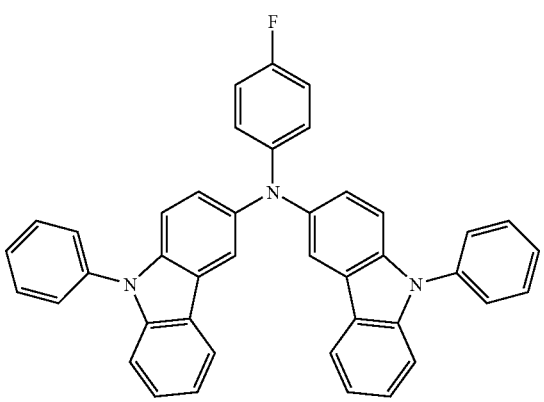
38
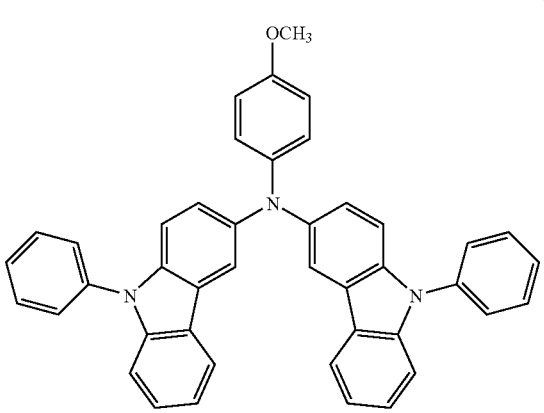

39
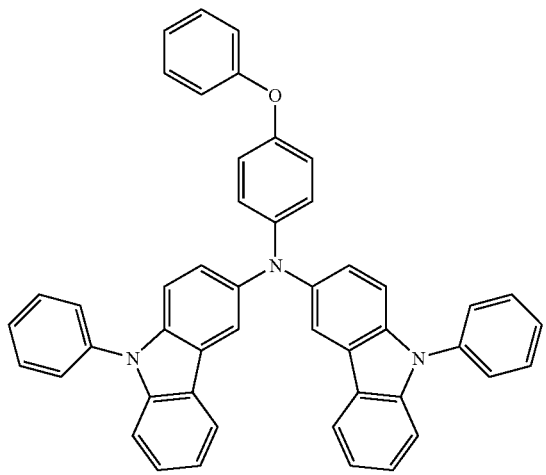
40
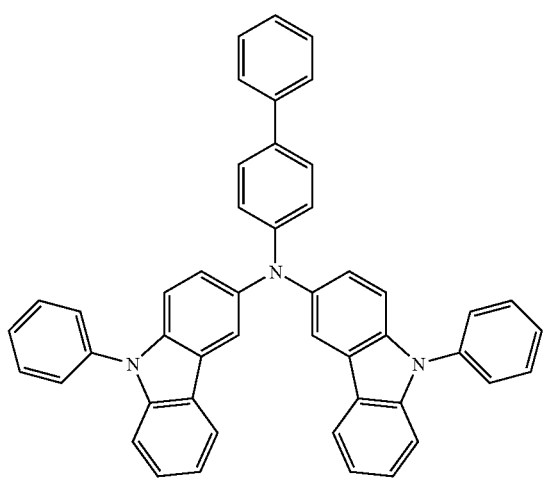
41
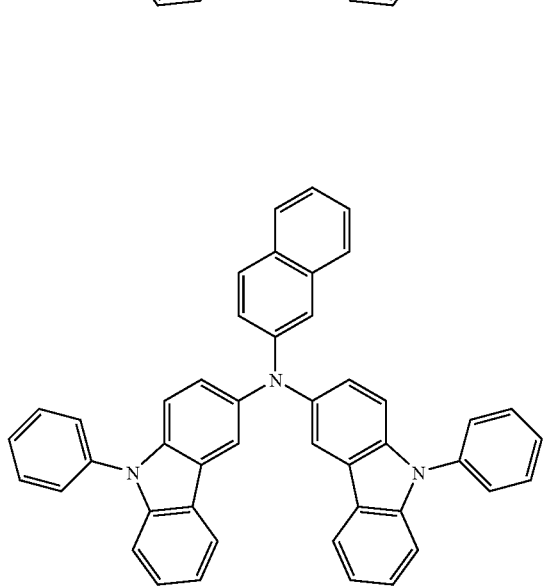
42
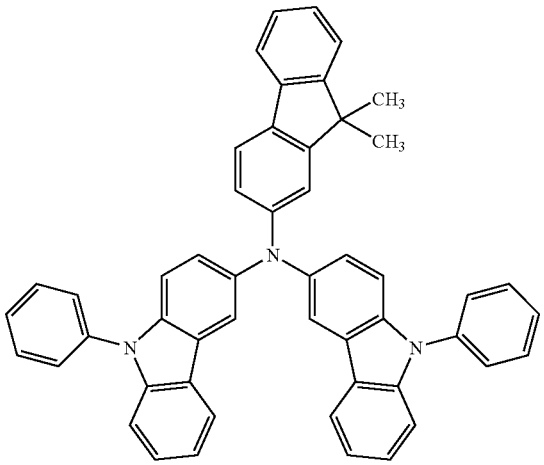
43
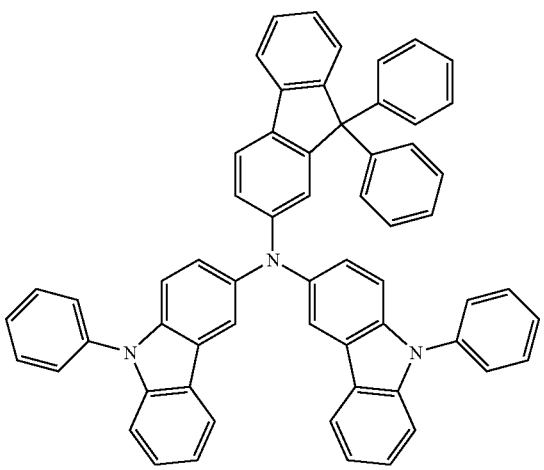
44
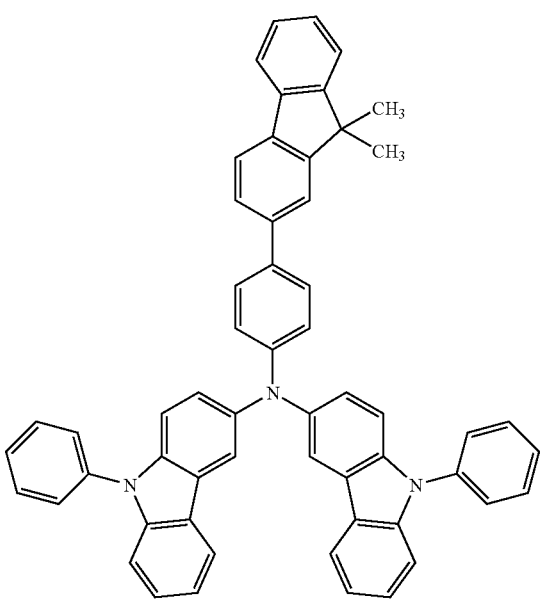

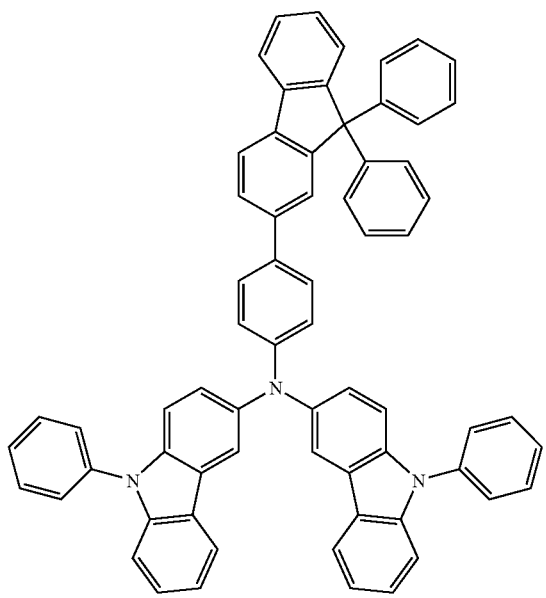
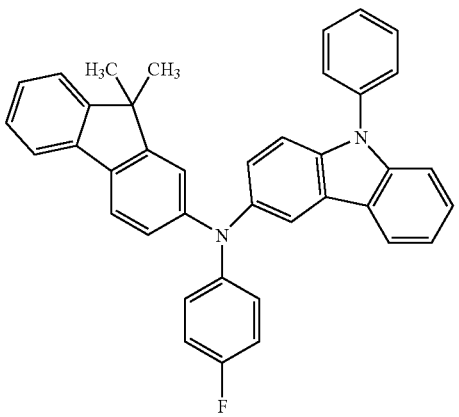
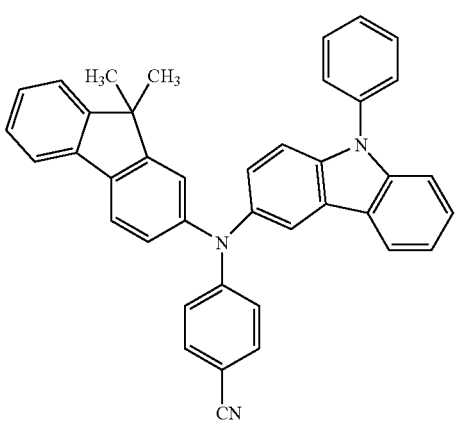
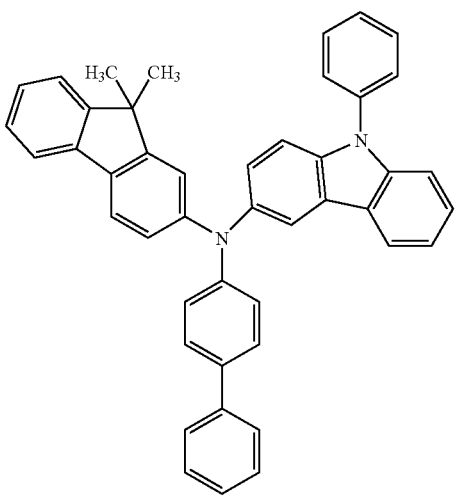

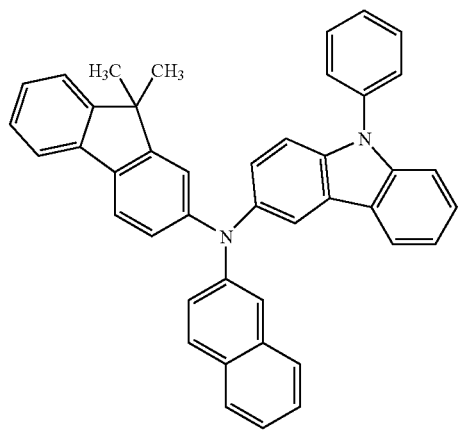
51
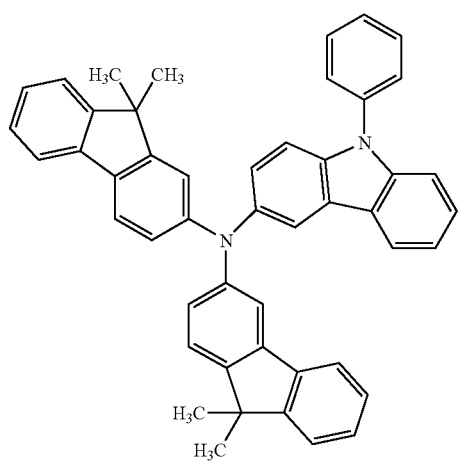
52
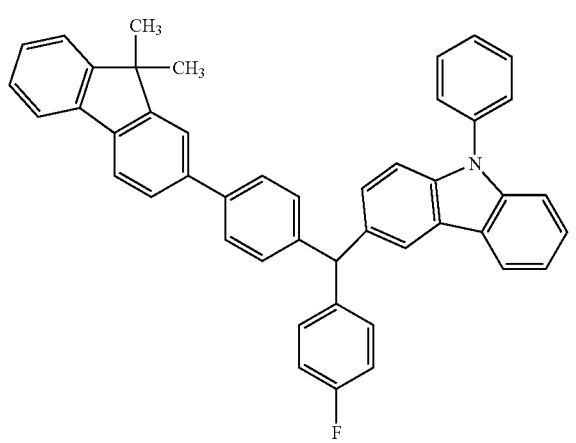
53
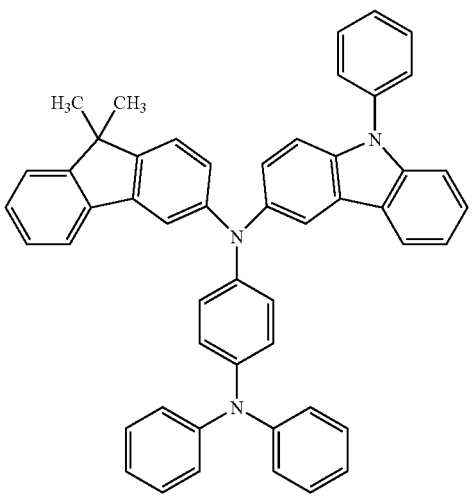
54
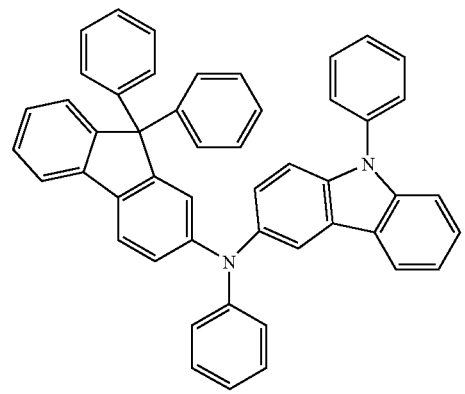
55
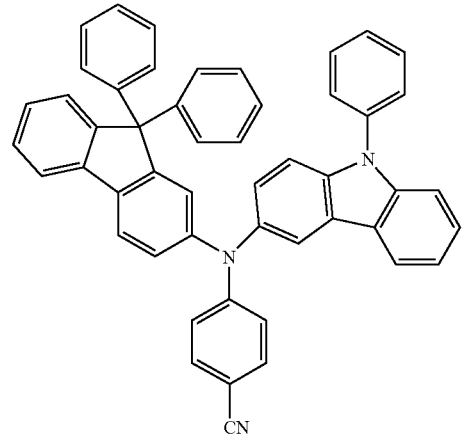
56

57
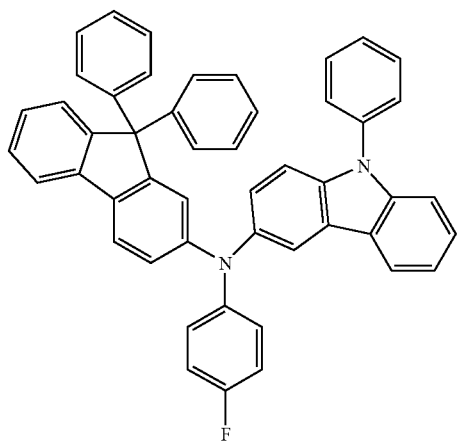
58
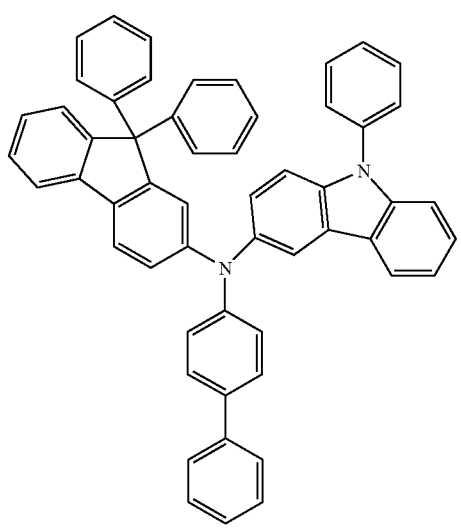
59
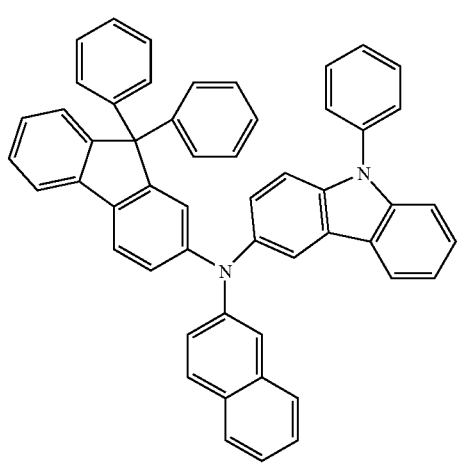
60
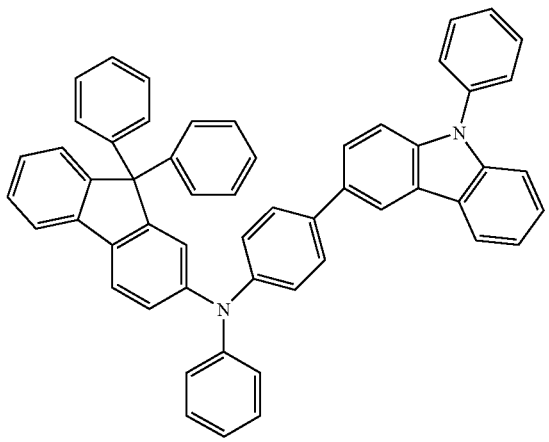
61
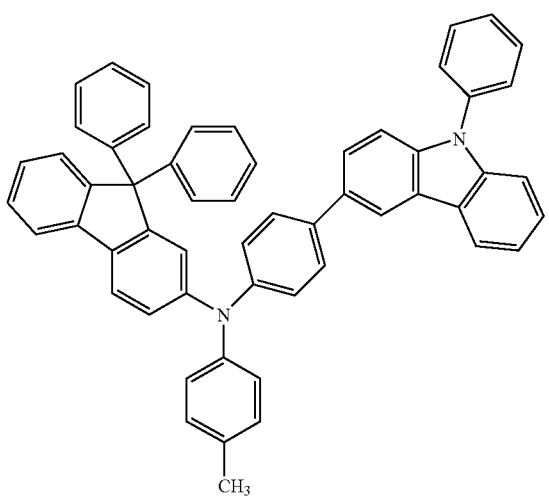
62
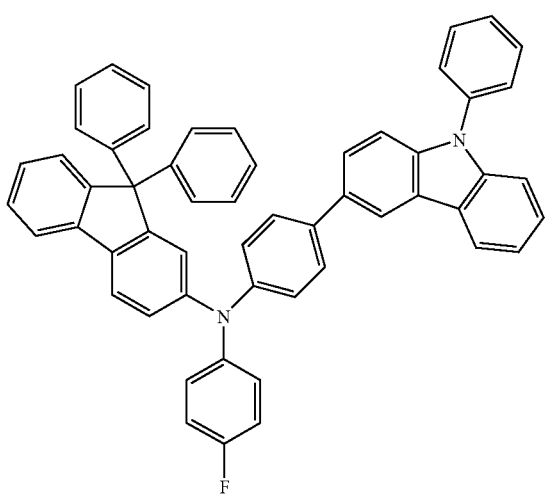

The compound represented by Formula 1 may be synthesized through a reaction between a phenylcarbazole (B') with a diamine (C') according to Reaction Scheme 1 below.

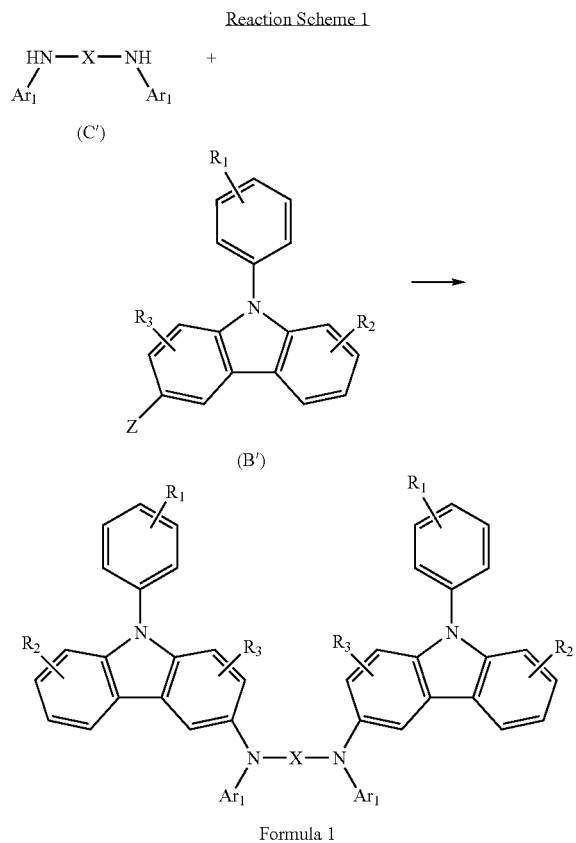

Here, X, $R_1$, $R_2$, $R_3$, and $Ar_1$ are already described above, and Z can be halogen, particularly iodine (I). The reaction can be performed in the presence of $Pd_2(dba)_3$ (dba=dibenzylideneacetone), sodium tert-butoxide and tri(tert-butyl)phosphine and at a reaction temperatures in the range of 50 to 150.

The layer which is included in the organic layer and which includes at least one of the compounds represented by Formulae 1, 2, and 3 may be a hole injection layer, a hole transport layer, or a single layer having hole injecting and transporting properties.

For example, the layer included in the organic layer and including at least one of the compounds represented by Formulae 1, 2, and 3 may be a hole injection layer.

The thickness of the hole injection layer formed under the red emission layer may be in the range of 1,600 to 2,200 Å, and preferably 1,900 to 2,200 Å. When the thickness of the hole injection layer formed under the red emission region is within the ranges described above, hole injecting and transporting properties suitable for causing resonance in a red emission layer of the organic layer can be obtained, and thus color purity, efficiency of the device, and a driving voltage of the device may be improved. In certain embodiments, the thickness of the hole injection layer formed under the red emission layer may be 1600, 1620, 1640, 1660, 1680, 1700, 1720, 1740, 1760, 1780, 1800, 1820, 1840, 1860, 1880, 1900, 1920, 1940, 1960, 1980, 2000, 2020, 2040, 2060, 2080, 2100, 2120, 2140, 2160, 2180, or 2200 Å. In some embodiments, the thickness of the hole injection layer formed under the red emission layer may be within a range defined by two of the foregoing thicknesses.

The thickness of the hole injection layer formed under the green emission region may be in the range of 1,400 to 1,800 Å, and preferably 1,600 to 1,800 Å. When the thickness of the hole injection layer is within the ranges described above, hole injecting and transporting properties suitable for causing resonance in a green emission layer of the organic layer can be obtained, and thus color purity, efficiency of the device, and the driving voltage of the device may be improved. In certain embodiments, the thickness of the hole injection layer formed under the green emission layer may be, 1400, 1420, 1440, 1460, 1480, 1500, 1520, 1540, 1560, 1580, 1600, 1620, 1640, 1660, 1680, 1700, 1720, 1740, 1760, 1780, or 1800 Å. In some embodiments, the thickness of the hole injection layer formed under the green emission layer may be within a range defined by two of the foregoing thicknesses.

The thickness of the hole injection layer formed under the blue emission region may be in the range of 1,000 to 1,400 Å, and preferably 1,100 to 1,300 Å. When the thickness of the hole injection layer formed under the blue emission region is within the ranges described above, hole injecting and transporting properties suitable for causing resonance in a blue emission layer of the organic layer can be obtained, and thus color purity, efficiency of the device, and the driving voltage of the device may be improved. In certain embodiments, the thickness of the hole injection layer formed under the blue emission layer may be, 1000, 1020, 1040, 1060, 1080, 1100, 1120, 1140, 1160, 1180, 1200, 1220, 1240, 1260, 1280, 1300, 1320, 1340, 1360, 1380, or 1400 Å. In some embodiments, the thickness of the hole injection layer formed under the blue emission layer may be within a range defined by two of the foregoing thicknesses.

The organic layer may further include a hole transport layer.

The total thickness of a region of the hole injection layer formed under a red emission region and the hole transport layer may be in the range of 2,000 to 2,400 Å, and preferably 2,100 to 2,300 Å. The thickness of the region of the hole injection layer formed under a red emission region may be in the range of 1,600 to 2,200 Å, and preferably 1,900 to 2,200 Å. When the total thickness of the region of the hole injection layer formed under the red emission region and the hole transport layer and/or the thickness of the region of the hole injection layer formed under the red emission region are within the ranges described above, hole injecting and transporting properties suitable for causing resonance in the red emission layer can be obtained, and thus color purity, efficiency of the device, and the driving voltage of the device may be improved. In certain embodiments, total thickness of a region of the hole injection layer formed under the red emission region and the hole transport layer may be, 2000, 2020, 2040, 2060, 2080, 2100, 2120, 2140, 2160, 2180, 2200, 2220, 2240, 2260, 2280, 2300, 2320, 2340, 2360, 2380, or 2400 Å. In some embodiments, the total thickness of the hole injection layer and the hole transport layer formed under the red emission layer may be within a range defined by two of the foregoing thicknesses.

The total thickness of a region of the hole injection layer formed under a green emission region and the hole transport layer may be in the range of 1,600 to 2,000 Å, and preferably 1,700 to 1,900 Å. The thickness of the region of the hole injection layer formed under the green emission region may be in the range of 1,400 to 1,800 Å, and preferably 1,600 to 1,800 Å. When the total thickness of the region of the hole injection layer formed under the green emission region and the hole transport layer and/or the thickness of the region of the hole injection layer formed under the green emission region are within the ranges described above, hole injecting and transporting properties suitable for causing resonance in the green emission layer can be obtained, and thus color purity, efficiency of the device, and a driving voltage of the device may be improved. In certain embodiments, total thickness of a region of the hole injection layer formed under the green emission region and the hole transport layer may be, 1600, 1620, 1640, 1660, 1680, 1700, 1720, 1740, 1760, 1780, 1800, 1820, 1840, 1860, 1880, 1900, 1920, 1940, 1960, 1980, or 2000 Å. In some embodiments, the total thickness of the hole injection layer and the hole transport layer formed under the green emission layer may be within a range defined by two of the foregoing thicknesses.

The total thickness of a region of the hole injection layer formed under a blur emission region and the hole transport layer may be in the range of 1,200 to 1,600 Å, and preferably 1,300 to 1,500 Å. The thickness of the region of the hole injection layer formed under the blur emission region may be in the range of 1,000 to 1,400 Å, and preferably 1,100 to 1,300 Å. When the total thickness of the region of the hole injection layer formed under the blur emission region and the hole transport layer and/or the thickness of the region of the hole injection layer formed under the blur emission region are within the ranges described above, hole injecting and transporting properties suitable for causing resonance in the blue emission layer can be obtained, and thus color purity, efficiency of the device, and the driving voltage of the device may be improved. In certain embodiments, total thickness of a region of the hole injection layer formed under the blue emission region and the hole transport layer may be, 1200, 1220, 1240, 1260, 1280, 1300, 1320, 1340, 1360, 1380, 1400, 1420, 1440, 1460, 1480, 1500, 1520, 1540, 1560, 1580, or 1600 Å. In some embodiments, the total thickness of the hole injection layer and the hole transport layer formed under the blue emission layer may be within a range defined by two of the foregoing thicknesses.

An organic light emitting device according to an embodiment of the present invention includes: a substrate; a first electrode; a second electrode; and an organic layer interposed between the first electrode and the second electrode and comprising an emission layer having a red emission region and a hole injection layer having a region formed under the red emission region, wherein one of the first electrode and the second electrode is a reflective electrode and the other is a semitransparent or transparent electrode, and wherein the thickness of the region of the hole injection layer formed under the red emission region is in the range of 1,600 to 2,200 Å, and preferably 1,900 to 2,200 Å.

When the thickness of the region of the hole injection layer formed under the red emission region is within the ranges described above, hole injecting and transporting properties suitable for causing resonance in a red emission layer can be obtained, and thus color purity, efficiency of the device, and the driving voltage of the device may be improved.

An organic light emitting device according to an embodiment of the present invention includes: a substrate; a first electrode; a second electrode; and an organic layer interposed between the first electrode and the second electrode and comprising an emission layer having a green emission region and a hole injection layer having a region formed under the green emission region, wherein one of the first electrode and the second electrode is a reflective electrode and the other is a semitransparent or transparent electrode, and wherein the thickness of the region of the hole injection layer formed under the green emission region is in the range of 1,400 to 1,800 Å, and preferably 1,600 to 1,800 Å.

When the thickness of the region of the hole injection layer formed under the green emission region is within the ranges described above, hole injecting and transporting properties suitable for causing resonance in the green emission layer can be obtained, and thus color purity, efficiency of the device, the driving voltage of the device may be improved.

An organic light emitting device according to an embodiment of the present invention includes: a substrate; a first electrode; a second electrode; and an organic layer interposed between the first electrode and the second electrode and comprising an emission layer having a blue emission region and a hole injection layer having a region formed under the blue emission region, wherein one of the first electrode and the second electrode is a reflective electrode and the other is a semitransparent or transparent electrode, and wherein the thickness of the region of the hole injection layer formed under the blue emission region is in the range of 1,000 to 1,400 Å, and preferably 1,100 to 1,300 Å.

When the thickness of the region of the hole injection layer formed under the blue emission region is within the ranges described above, hole injecting and transporting properties suitable for causing resonance in the blue emission layer can be obtained, and thus color purity, efficiency of the device, and the driving voltage of the device may be improved.

Resonance can occur between the first electrode and the second electrode of an organic light emitting device according to an embodiment of the present invention during the operation thereof. The hole injection layer of the organic layer disposed between the first electrode and the second electrode may have a specific thickness according to the color of the light emitted by the organic layer described above to obtain excellent properties such as driving voltage, current density, luminance, color purity, efficiency and lifetime of the organic light emitting device.

In an organic light emitting device according to an embodiment of the present invention, the first electrode can be formed on the substrate. The first electrode may be a reflective electrode and the second electrode may be a semitransparent or transparent electrode. Thus, resonance may occur between the first electrode and the second electrode during the operation of the device. Accordingly, the light generated in the organic layer between the first electrode and the second electrode resonates between the first electrode and the second electrode during the operation of the organic light emitting device, and the light is extracted through the second electrode, that is, in a direction away from the substrate.

The organic layer of the organic light emitting device may include an emission layer and/or a hole injection layer. The organic layer may further include at least one of a hole transport layer, an electron blocking layer, a hole blocking layer, an electron transport layer, and an electron injection layer. Thus, for example, an organic light emitting device according to an embodiment of the present invention may have a structure of substrate/first electrode/hole injection layer (HIL)/hole transport layer (HTL)/emission layer (EML)/hole blocking layer (HBL)/electron transport layer (ETL)/electron injection layer (EIL)/second electrode as illustrated in FIG. 1.

Figure 2:
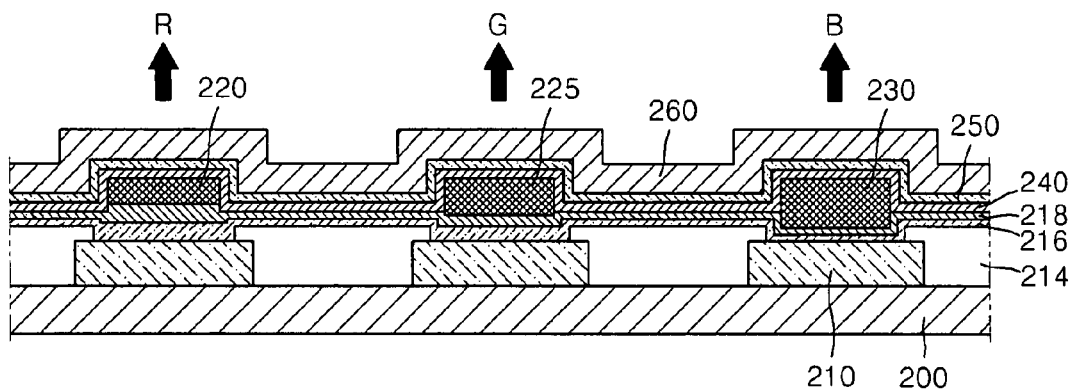
FIG. 2 schematically illustrates an organic light emitting device including an emission layer comprised of a red emission region, a green emission region, and blue emission region according to an embodiment of the present invention.

Hereinafter, Examples and methods of manufacturing an organic light emitting device according to an embodiment of the present invention will be described with reference to the organic light emitting device illustrated in FIGS. 1 and 2. FIG. 1 schematically illustrates a structure of an organic light emitting device according to an embodiment of the present invention. FIG. 2 schematically illustrates an organic light emitting device including red, green, and blue emission layers according to an embodiment of the present invention.

Referring to FIG. 2, a first electrode 210 is formed on a substrate 200. Here, the substrate 200, which can be any substrate that is commonly used in conventional organic light emitting devices, may be a glass substrate or a plastic substrate with excellent transparency, surface smoothness, ease of treatment, and that is waterproof.

The first electrode 210 may be a reflective electrode, a semitransparent electrode or a transparent electrode formed of a metal with excellent conductivity such as Li, Mg, Al, Al—Li, Ca, Mg—In, Mg—Ag, and Ca—Al, or a metal oxide with excellent conductivity such as ITO, IZO, and $IN_2O_3$. A combination of two or more of the metals or the metal oxides described above can also be used.

Then a pixel defining layer 214 which defines regions in which red, green, and blue emission layers will be formed is formed on predetermined regions. The pixel defining layer 214 can be formed by deposition or coating, etc. using inorganic materials such as a silicon oxide and a nitride or organic materials having insulating properties.

Then, a HIL 216 and a HTL 218 are sequentially formed on the first electrode 210 by thermal evaporation or spin coating according to regions which are defined by the pixel defining layer 214.

The HIL 216 may include at least one of the compounds represented by Formulae 1, 2, and 3. The HTL 218 may include 1,3,5-tricarbazolylbenzene, 4,4'-biscarbazolylbiphenyl, polyvinylcarbazole, m-biscarbazolylphenyl, 4,4'-biscarbazolyl-2,2'-dimethylbiphenyl, 4,4',4''-tri(N-carbazolyl) triphenylamine, 1,3,5-tri(2-carbazolylphenyl)benzene, 1,3,5-tris(2-carbazolyl-5-methoxyphenyl)benzene, bis(4-carbazolylphenyl)silane, N,N'-bis(3-methylphenyl)-N,N'-diphenyl-[1,1-biphenyl]-4,4'-diamine (TPD), N,N'-di(naphthalene-1-yl)-N,N'-diphenylbenzidine (α-NPD), N,N'-diphenyl-N,N'-bis(1-naphthyl)-(1,1'-biphenyl)-4,4'-diamine (NPB), IDE 320 (Id emitsu Corporation), poly(9,9-dioctylfluorene-co-N-(4-butylphenyl)diphenylamine (TFB), or poly(9,9-dioctylfluorene-co-bis-(4-butylphenyl-bis-N,N-phenyl-1,4-phenylenediamin (PFB), but is not limited to the above-described examples.

The thickness of the HIL 216 and the HTL 218 are described above.

The HIL 216 can be formed using a known method such as vacuum deposition, spin coating, casting, Langmuir Blodgett (LB), or the like.

When the HIL 216 is formed by vacuum deposition, vacuum deposition conditions may vary according to a compound that is used to form the HIL 216, and the structure and thermal properties of the HIL 216 to be formed. In general, however, conditions for vacuum deposition may include a deposition temperature of 100-500° C., a pressure of $10^{-8}$-$10^{-3}$ torr, and a deposition speed of 0.01-100 Å/sec.

When the HIL 216 is formed by spin coating, coating conditions may vary according to a compound that is used to form the HIL 216, and the structure and thermal properties of the HIL 216 to be formed. In general, however, the coating speed may be in the range of about 2000 to 5000 rpm, and a temperature for heat treatment, which is performed to remove a solvent after coating may be in the range of about 80 to 200° C.

The HTL 218 can be formed using a known method such as vacuum deposition, spin coating, casting, LB, or the like.

When the HTL 218 is formed by vacuum deposition and spin coating, conditions for deposition and coating are similar to those for formation of the HIL 216, although conditions for deposition and coating may vary according to a material that is used to form the HTL 218.

Red, green and blue EMLs, 220, 225, and 230 are formed on the HTL 218. The material used to form the red, green and blue EMLs, 220, 225, and 230 is not limited.

For example, DCM1, DCM2, Eu(thenoyltrifluoroacetone) 3 (Eu(TTA)3), and butyl-6-(1,1,7,7,-tetramethyljulolidyl-9-enyl)-4H-pyran (DCJTB) can be used to form the red EML 220. Alternatively, a dopant such DCJTB can be deposited with Alq3, Alq3 and rubrene can be co-deposited and a dopant can be deposited thereon, or dopants such as BTPIr or RD 61 can be deposited with 4,4'-N—N'-dicarbazole-biphenyl (CBP) to form the red EML 220, but the present invention is not limited to the above-described examples.

For example, Coumarin 6, C545T, quinacridone, and Ir(ppy)₃ can be used to form the green EML 225. Alternatively, a dopant such Ir(ppy)₃ can be deposited with CBP, or a dopant such as a coumarin-based material can be deposited with Alq3 as a host to form the green EML 225, but the present invention is not limited to the above-described examples. Examples of the coumarin-based dopant may include C314S, C343S, C7, C7S, C6, C6S, C314T, and C545T.

For example, oxadiazole dimer dyes (Bis-DAPOXP), spiro compounds (Spiro-DPVBi, Spiro-6P), triarylamine compounds, bis(styryl)amine (DPVBi, DSA), CzTT, Anthracene, TPB, PPCP, DST, TPA, OXD-4, BBOT, AZM-Zn, and BH-013X (Idemitsu Corporation) which is an aromatic hydrocarbon compound containing a naphthalene moiety can be used to form the blue EML 230. Alternatively, a dopant such IDE 105 (Idemitsu Corporation) can be deposited on IDE 140 (Idemitsu Corporation) to form the blue EML 230, but the present invention is not limited to the above-described examples.

The thickness of the red, green and blue EMLs, 220, 225 and 230 may be in the range of 200 to 500 Å, and preferably 300 to 400 Å. The thickness of each of the red, green and blue, EMLs, 220, 225 and 230 may be the same or different. When the thickness of the red, green and blue, EMLs, 220, 225 and 230 is within the ranges described above, excellent lifetime and driving voltage of the light emitting device may be obtained.

The red, green and blue, EMLs, 220, 225 and 230 can be formed using a known method such as vacuum deposition, spin coating, casting, LB, or the like. When the red, green and blue, EMLs, 220, 225 and 230 are formed by vacuum deposition and spin coating, conditions for deposition and coating are similar to those for formation of the HIL 216, although conditions for deposition and coating may vary according to the material that is used to form the red, green and blue, EMLs, 220, 225 and 230.

A HBL (not shown) can optionally be formed on the red, green and blue, EMLs, 220, 225 and 230 by vacuum deposition or spin coating. A material that is used to form the HBL should have a capability of transporting electrons and an ionization potential higher than the red, green and blue, EMLs, 220, 225 and 230, and thus examples of the material may include bis(2-methyl-8-quinolato)-(p-phenylphenolato)-aluminum (Balq), bathocuproine (BCP), and tris(N-aryl benzimidazole) (TPBI), but are not limited thereto.

The thickness of the HBL may be in the range of 30 to 60 Å, and preferably 40 to 50 Å. When the thickness of the HBL is within the ranges described above, a proper hole blocking capability and the driving voltage of the device may be obtained.

The HBL can be formed using a known method such as vacuum deposition, spin coating, casting, LB, or the like. When the HBL is formed by vacuum deposition and spin coating, conditions for deposition and coating are similar to those for formation of the HIL 216, although conditions for deposition and coating may vary according to the material that is used to form the HBL.

An ETL 240 can be optionally formed by vacuum deposition or spin coating on the red, green and blue, EMLs, 220, 225 and 230, or the HBL. The material that is used to form the ETL 240 may be Alq3, but is not limited thereto.

The thickness of the ETL 240 may be in the range of about 100 to 400 Å, and preferably, 250 to 350 Å. When the thickness of the ETL 240 is greater than 100 Å, proper charge balance can be maintained. On the other hand, when the thickness of the ETL 240 is less than 400 Å, proper driving voltage of the device may be obtained.

The ETL 240 can be formed using a known method such as vacuum deposition, spin coating, casting, LB, or the like. When the ETL 240 is formed by vacuum deposition and spin coating, conditions for deposition and coating are similar to those for formation of the HIL 216, although conditions for deposition and coating may vary according to the material that is used to form the ETL 240.

An EIL 250 may be formed by vacuum deposition or spin coating on the ETL 240. The material that is used to form the EIL 250 may be $BaF_2$, LiF, NaCl, CsF, $Li_2O$, BaO, Liq, or the like, but is not limited thereto.

The thickness of the EIL 250 may be in the range of 2 to 100 Å, preferably, 2 to 5 Å, and more preferably 2 to 4 Å. When the thickness of the EIL 250 is within the ranges described above, proper electron injecting capability and the driving voltage of the device may be obtained.

The EIL 250 can be formed using a known method such as vacuum deposition, spin coating, casting, LB, or the like. When the EIL 250 is formed by vacuum deposition and spin coating, conditions for deposition and coating are similar to those for formation of the HIL 216, although conditions for deposition and coating may vary according to the material that is used to form the EIL 250.

A second electrode 260 is formed on the EIL 250 by deposition to thereby complete the manufacture of the organic light-emitting device according to the current embodiment of the present invention.

The material that is used to form the second electrode 260 can be a transparent metal oxide with excellent conductivity such as ITO, IZO, $SnO_2$, and ZnO. Li, Mg, Al, Al—Li, Ca, Mg—In, Mg—Ag, Ca—Al can be used to form a thin film of the second electrode 260, and thus the second electrode 260 can be a reflective electrode, a semitransparent electrode, or a transparent electrode in a various manner. The material used to form the second electrode 260 is not limited to the above-described examples.

The first electrode 210 and the second electrode 260 can be an anode or a cathode.

The organic light emitting device according to the current embodiment of the present invention can be utilized in various types of flat panel display devices such as a passive matrix organic light emitting device and an active matrix organic light emitting device. When the organic light emitting device of the present embodiment is utilized in an active matrix organic light emitting device, the first electrode 210 as a pixel electrode that is formed on the substrate 200 can be electrically connected to a source electrode or a drain electrode of a thin film transistor. The organic light emitting device of the present embodiment can also be utilized in a flat panel display that can realize images in two sides.

Hereinafter, the present invention will be described more specifically with reference to the following Synthesis Examples of Compounds 8, 9, 10, 11, 14, 28, 35, and 56 and Examples of an organic light emitting device according to an embodiment of the present invention will now be described in detail. However, the Synthesis Examples and the Examples are not intended to limit the scope of the present invention.

EXAMPLES

Synthesis Example 1

Synthesis of Compound 8

Compound 8 was synthesized through Reaction Scheme 2 below.

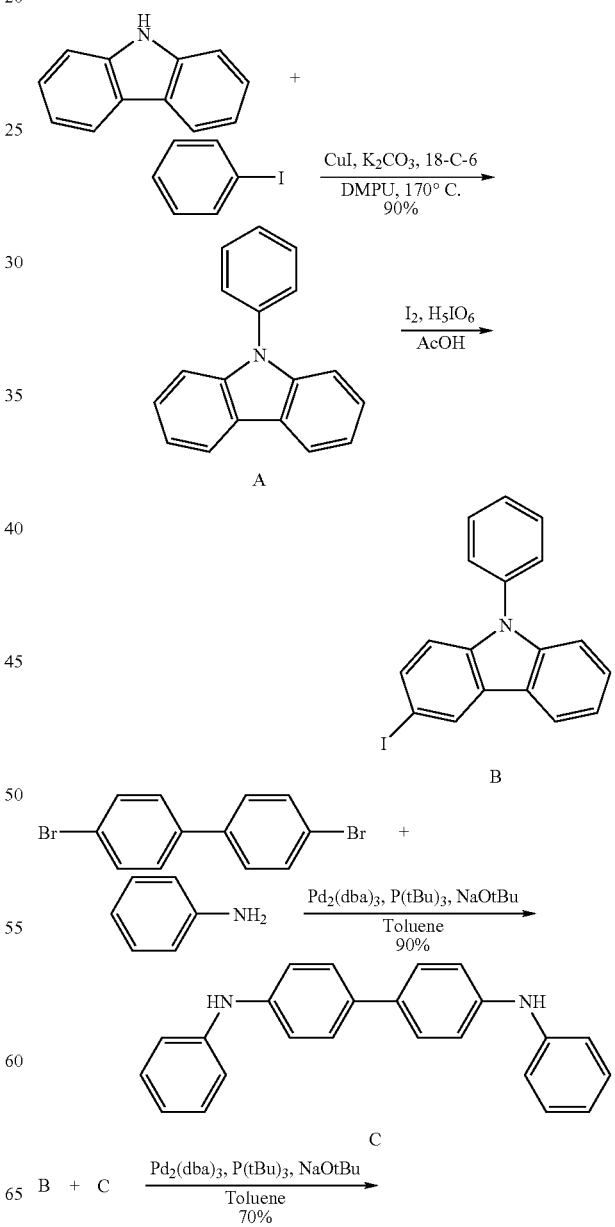

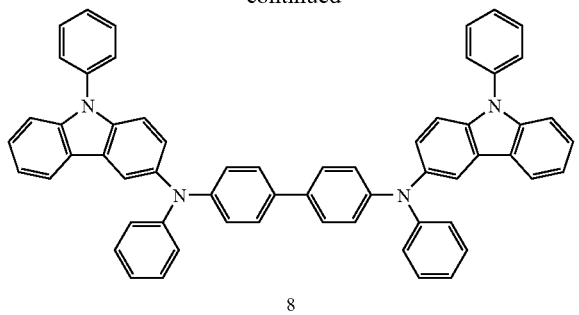

8

Synthesis of Intermediate A 16.7 g (100 mmol) of carbazole, 26.5 g (130 mmol) of iodobenzene, 1.9 g (10 mmol) of CuI, 138 g (1 mol) of $K_2CO_3$, and 530 mg (2 mmol) of 18-crown-6 were dissolved in 500 ml of 1,3-Dimethyl-3,4,5,6-tetrahydro-(1H)-pyrimidinone (DMPU), and heated at 170° C. for 8 hours.

After the reaction terminated, the reaction mixture was cooled to room temperature, and the resultant solid substance was filtered. Then a small amount of ammonium hydroxide was added to the filtered solution. The resultant was washed three times with 300 ml of diethylether, and dried in $MgSO_4$ under reduced pressure. As a result, a crude product was obtained. The crude product was purified using a silica gel column chromatography to produce 22 g of Intermediate A as a white solid (yield 90%).

$^1$H NMR ($CDCl_3$, 400 MHz) δ (ppm) 8.12 (d, 2H), 7.58-7.53 (m, 4H), 7.46-7.42 (m, 1H), 7.38 (d, 4H), 7.30-7.26 (m, 2H); $^{13}$C NMR ($CDCl_3$, 100 MHz) δ (ppm) 141.0, 137.9, 130.0, 127.5, 127.3, 126.0, 123.5, 120.4, 120.0, 109.9.

Synthesis of Intermediate B 2.433 g (10 mmol) of Intermediate A was added to 100 ml of 80% acetic acid. 1.357 g (5.35 mmol) of iodine ($I_2$) and 0.333 g (1.46 mmol) of o-periodic acid ($H_5IO_6$) were added thereto in the solid state. Then, the mixture was stirred at 80° C. in a nitrogen atmosphere for 2 hours.

After the reaction terminated, the resultant solution was extracted three times with 50 ml of ethylether. An organic layer collected from the mixture was dried over $MgSO_4$ to evaporate the solvent. As a result, the dried result was purified using a silica gel column chromatography to produce 3.23 g of Intermediate B as a white solid (yield 87%).

$^1$H NMR ($CDCl_3$, 300 MHz) δ (ppm) 8.43 (d, 1H), 8.05 (d, 1H), 7.62 (dd, 1H), 7.61-7.75 (m, 2H), 7.51-7.43 (m, 3H), 7.41-7.35 (m, 2H), 7.27 (dd, 1H), 7.14 (d, 1H)

Synthesis of Intermediate C 3.12 g (10 mmol) of 4,4'-dibromodiphenyl, 2.3 ml (25 mmol) of aniline, 2.9 g (30 mmol) of t-BuONa, 183 mg (0.2 mmol) of $Pd_2(dba)_3$, 20 mg (0.1 mmol) of $P(t-Bu)_3$ were dissolved in 30 ml of toluene and the mixture was stirred at 90° C. for 3 hours.

The reaction mixture was cooled to room temperature, and the resultant solution was extracted three times with 30 ml of distilled water and diethylether. A precipitate in an organic layer was filtered, washed with acetone and diethylether, and dried in a vacuum condition to produce 0.3 g of Intermediate C (yield 90%).

Intermediate C was identified by $^1$H-NMR.

$^1$H NMR (DMSO-$d_6$, 400 MHz) δ (ppm) 8.22 (s, 2H), 7.48 (d, 4H), 7.23 (t, 4H), 7.10 (dd, 8H), 6.82 (t, 2H); $^{13}$C NMR (DMSO-$d_6$, 100 MHz) δ (ppm) 145.7, 144.3, 133.7, 131.4, 128.7, 121.2, 119.2, 118.9.

Synthesis of Compound 8

912 mg (2.47 mmol) of Intermediate B, 336.4 mg (1 mmol) of Intermediate C, 300 mg (3 mmol) of t-BuONa, 40 mg (0.02 mmol) of $Pd_2(dba)_3$, 3 mg (0.01 mmol) of $P(t-Bu)_3$ were dissolved in 5 ml of toluene and the mixture was stirred at 90° C. for 3 hours.

After the reaction terminated, the resultant mixture was cooled to room temperature, and the resultant solution was extracted three times with distilled water and 30 ml of ethylether. An organic layer collected from the mixture was dried over $MgSO_4$ to evaporate the solvent. As a result, the dried result was purified using a silica gel column chromatography to produce 570 mg of Compound 8 as a yellow solid (Yield 70%).

$^1$H NMR ($CDCl_3$, 300 MHz) δ (ppm) 7.99 (d, 2H), 7.95 (s, 2H), 7.61-7.57 (m, 8H), 7.48-7.32 (m, 12H), 7.27-7.19 (m, 8H), 7.18-7.10 (m, 8H), 6.96 (t, 2H); $^{13}$C NMR ($CDCl_3$, 100 MHz) δ (ppm) 148.4, 147.3, 141.3, 140.4, 138.0, 137.6, 133.9, 129.9, 129.1, 127.4, 127.1, 127.0, 126.1, 125.6, 124.3, 123.0, 122.9, 122.8, 121.7, 120.5, 119.9, 118.5, 110.7, 109.9.

Compound 8 was diluted in $CHCl_3$ to a concentration of 0.2 mM and a UV Spectrum of the diluted Compound 8 was obtained. Maximum absorption wavelengths were 353, 306 and 238 nm.

Td (decomposition temperature) and Tg (glass transition temperature) of Compound 8 were measured by performing thermal analysis using thermo gravimetric analysis (TGA) and differential scanning calorimetry (DSC) under the following conditions: $N_2$ atmosphere, temperatures of room temperature to 600° C. (10° C./min)-TGA and of room temperature to 400° C.-DSC, and Pan Type: Pt Pan in disposable Al Pan (TGA) and disposable Al pan (DSC). The measured Td was 494° C. and Tg was 153° C.

A highest occupied molecular orbital (HOMO) level of 5.16 eV and a lowest occupied molecular orbital (LUMO) level of 2.16 eV were obtained using AC-2 that measures UV absorption spectrum and ionization potential.

Synthesis Example 2

Synthesis Compound 9

Compound 9 was synthesized through Reaction Scheme 3 below.

Reaction Scheme 3

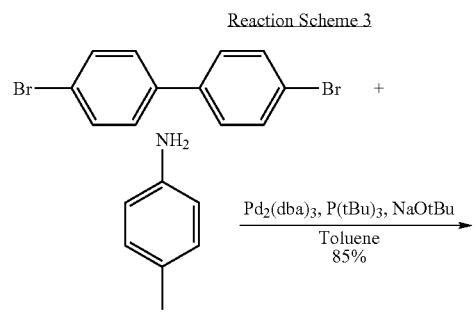

$Pd_2(dba)_3$, $P(tBu)_3$, NaOtBu

Toluene
85%

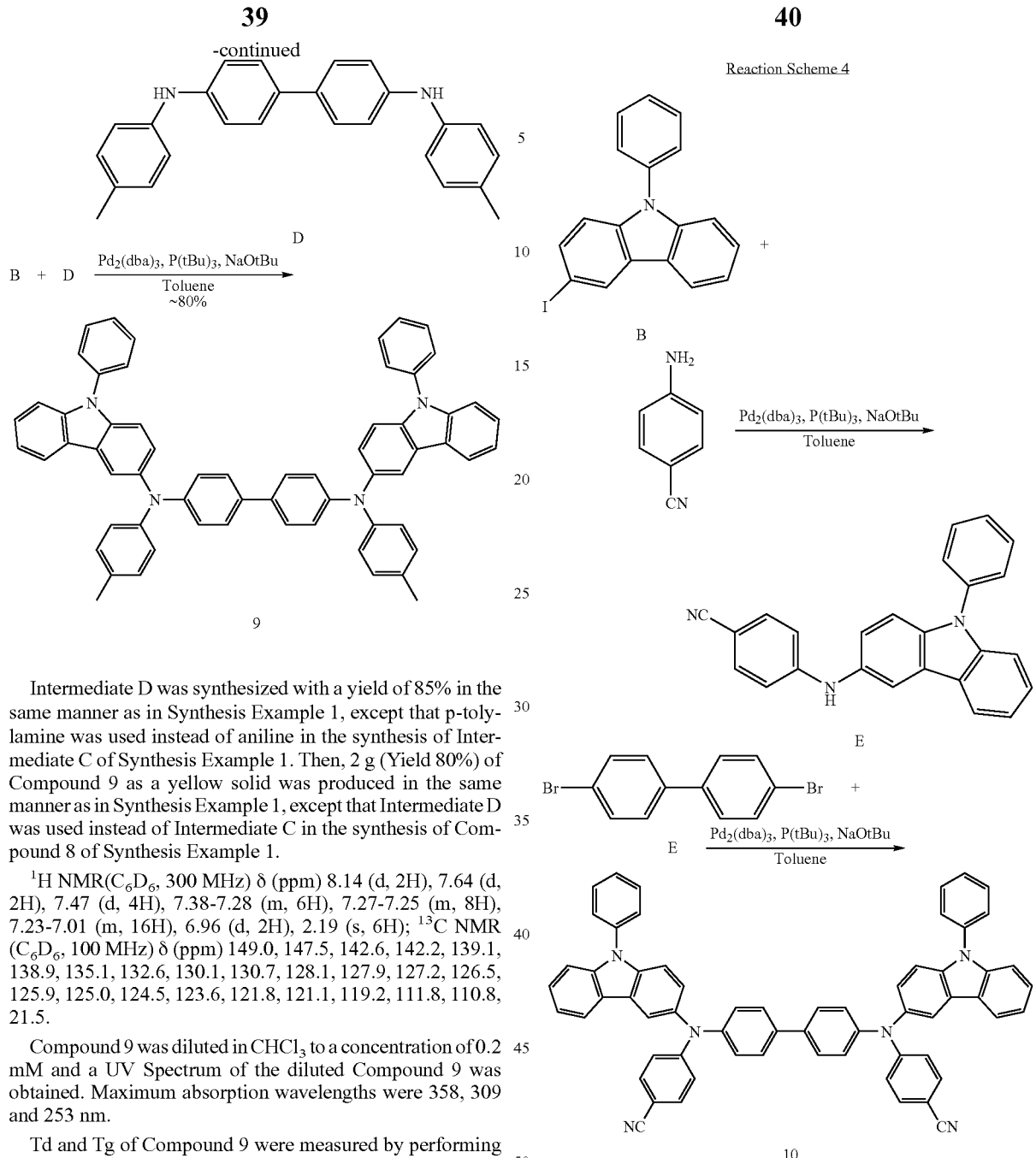

Intermediate D was synthesized with a yield of 85% in the same manner as in Synthesis Example 1, except that p-tolylamine was used instead of aniline in the synthesis of Intermediate C of Synthesis Example 1. Then, 2 g (Yield 80%) of Compound 9 as a yellow solid was produced in the same manner as in Synthesis Example 1, except that Intermediate D was used instead of Intermediate C in the synthesis of Compound 8 of Synthesis Example 1.

$^1$H NMR($C_6D_6$, 300 MHz) δ (ppm) 8.14 (d, 2H), 7.64 (d, 2H), 7.47 (d, 4H), 7.38-7.28 (m, 6H), 7.27-7.25 (m, 8H), 7.23-7.01 (m, 16H), 6.96 (d, 2H), 2.19 (s, 6H); $^{13}$C NMR ($C_6D_6$, 100 MHz) δ (ppm) 149.0, 147.5, 142.6, 142.2, 139.1, 138.9, 135.1, 132.6, 130.1, 130.7, 128.1, 127.9, 127.2, 126.5, 125.9, 125.0, 124.5, 123.6, 121.8, 121.1, 119.2, 111.8, 110.8, 21.5.

Compound 9 was diluted in $CHCl_3$ to a concentration of 0.2 mM and a UV Spectrum of the diluted Compound 9 was obtained. Maximum absorption wavelengths were 358, 309 and 253 nm.

Td and Tg of Compound 9 were measured by performing thermal analysis using TGA and DSC under the following conditions: $N_2$ atmosphere, temperatures of room temperature to 600° C. (10° C./min)-TGA and of room temperature to 400° C.-DSC, and Pan Type: Pt Pan in disposable Al Pan (TGA) and disposable Al pan (DSC). The measured Td was 480° C. and Tg was 155° C.

A HOMO level of 5.0 eV and a LUMO level of 2.02 eV were obtained using AC-2 that measures UV absorption spectrum and ionization potential.

Synthesis Example 3

Synthesis Compound 10

Compound 10 was synthesized through Reaction Scheme 4 below.

Synthesis of Intermediate E 3.69 g (10 mmol) of Intermediate B, 1.42 g (12 mmol) of 4-aminobenzonitril, 1.44 g (15 mmol) of t-BuONa, 183 mg (0.2 mmol) of $Pd_2(dba)_3$, and 40 mg (0.2 mmol) of $P(t-Bu)_3$ were dissolved in 50 ml of toluene and the mixture was stirred at 90° C. for 3 hours.

After the reaction terminated, the resultant mixture was cooled to room temperature, and the resultant solution was extracted three times with distilled water and 50 ml of diethylether. An organic layer collected from the mixture was dried over $MgSO_4$ to evaporate the solvent. As a result, the dried result was purified using a silica gel column chromatography to produce 1.8 g of Intermediate E (Yield 50%).

Synthesis of Compound 10

2.2 g (Yield 86%) of Compound 10 as a yellow solid was produced in the same manner as in Synthesis Example 1, except that Intermediate E and 4,4'-dibromodiphenyl were used instead of Intermediates B and C in the synthesis of Compound 8 of Synthesis Example 1.

$^1$H NMR (CDCl$_3$, 300 MHz) δ (ppm) 8.02 (d, 2H), 7.97 (d, 2H), 7.64-7.48 (m, 14H), 7.43-7.39 (m, 10H), 7.29-7.22 (m, 8H), 7.03 (d, 4H); $^{13}$C NMR (CDCl$_3$, 100 MHz) δ (ppm) 152.1, 145.6, 141.5, 138.9, 138.2, 137.3, 136.3, 133.2, 130.0, 127.9, 127.8, 127.0, 126.6, 125.8, 125.5, 124.6, 122.7, 120.5, 120.2, 119.9, 119.4, 118.9, 111.2, 110.1, 101.8.

Compound 10 was diluted in CHCl$_3$ to a concentration of 0.2 mM and a UV Spectrum of the diluted Compound 10 was obtained. Maximum absorption wavelengths were 304 and 238 nm.

Td, Tg and Tm of Compound 10 were measured by performing thermal analysis using TGA and DSC under the following conditions: N$_2$ atmosphere, temperatures of room temperature to 600° C. (10° C./min)-TGA and of room temperature to 400° C.-DSC, and Pan Type: Pt Pan in disposable Al Pan (TGA) and disposable Al pan (DSC). The measured Td was 492° C., Tg was 178° C., and Tm was 263° C.

A HOMO level of 5.4 eV and a LUMO level of 2.47 eV were obtained using AC-2 that measures UV absorption spectrum and ionization potential.

Synthesis Example 4

Synthesis Compound 11

Compound 11 was synthesized through Reaction Scheme 5 below.

Reaction Scheme 5

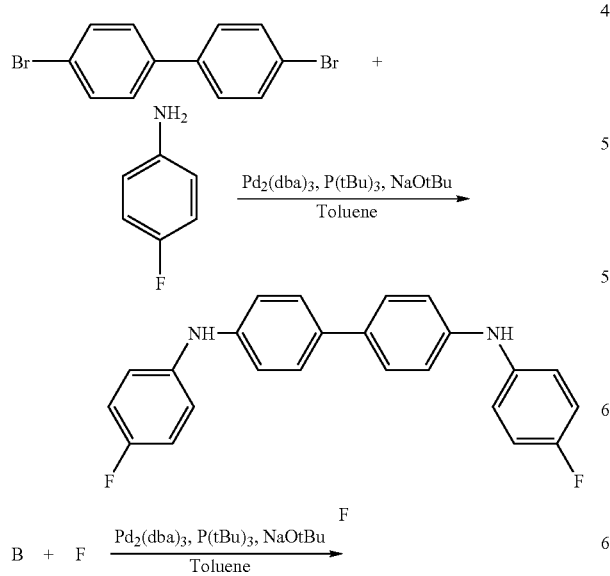

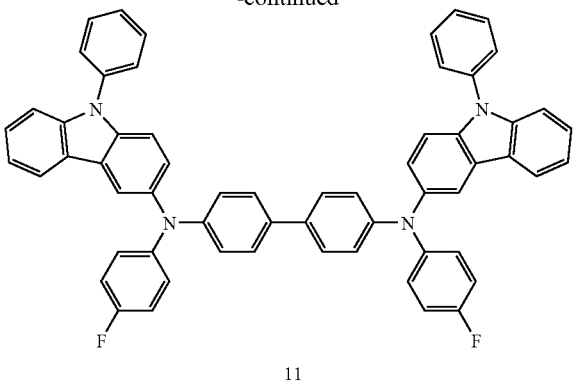

11

Intermediate F was synthesized with a yield of 95% in the same manner as in Synthesis Example 1, except that 4-fluorophenylamine was used instead of aniline in the synthesis of Intermediate C of Synthesis Example 1. Then, 1.8 g (Yield 84%) of Compound 11 as a yellow solid was produced in the same manner as in Synthesis Example 1, except that Intermediate F was used instead of Intermediate C in the synthesis of Compound 8 of Synthesis Example 1.

$^1$H NMR(C$_6$D$_6$, 300 MHz) δ (ppm) 8.05 (s, 2H), 7.68 (d, 2H), 7.48 (d, 4H), 7.29-7.11 (m, 22H), 7.09-7.01 (m, 6H), 6.78 (t, 4H)

Compound 11 was diluted in CHCl$_3$ to a concentration of 0.2 mM and UV Spectrum of the diluted Compound 11 was obtained. Maximum absorption wavelengths were 351, 297 and 248 nm.

Td, Tg, and Tm of Compound 11 were measured by performing thermal analysis using TGA and DSC under the following conditions: N$_2$ atmosphere, temperatures of room temperature to 600° C. (10° C./min)-TGA and of room temperature to 400° C.-DSC, and Pan Type: Pt Pan in disposable Al Pan (TGA) and disposable Al pan (DSC). The measured Td was 464° C., Tg was 151° C., and Tm was 299° C.

A HOMO level of 5.1 eV and a LUMO level of 2.28 eV were obtained using AC-2 that measures UV absorption spectrum and ionization potential.

Synthesis Example 5

Synthesis Compound 14

Compound 14 was synthesized through Reaction Scheme 6 below.

Reaction Scheme 6

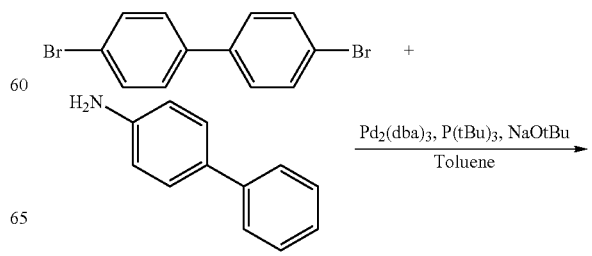

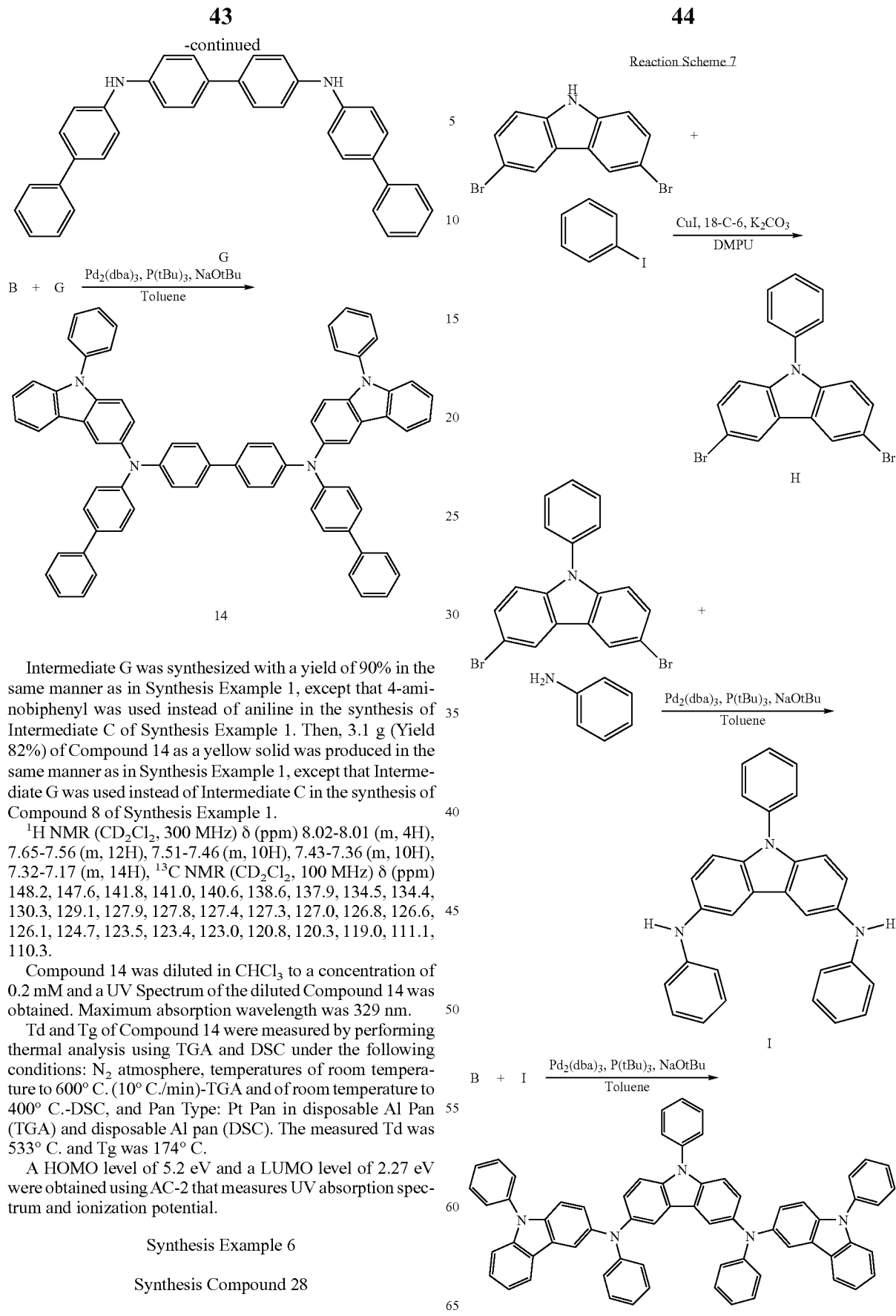

Intermediate G was synthesized with a yield of 90% in the same manner as in Synthesis Example 1, except that 4-aminobiphenyl was used instead of aniline in the synthesis of Intermediate C of Synthesis Example 1. Then, 3.1 g (Yield 82%) of Compound 14 as a yellow solid was produced in the same manner as in Synthesis Example 1, except that Intermediate G was used instead of Intermediate C in the synthesis of Compound 8 of Synthesis Example 1.

$^1$H NMR (CD$_2$Cl$_2$, 300 MHz) δ (ppm) 8.02-8.01 (m, 4H), 7.65-7.56 (m, 12H), 7.51-7.46 (m, 10H), 7.43-7.36 (m, 10H), 7.32-7.17 (m, 14H), $^{13}$C NMR (CD$_2$Cl$_2$, 100 MHz) δ (ppm) 148.2, 147.6, 141.8, 141.0, 140.6, 138.6, 137.9, 134.5, 134.4, 130.3, 129.1, 127.9, 127.8, 127.4, 127.3, 127.0, 126.8, 126.6, 126.1, 124.7, 123.5, 123.4, 123.0, 120.8, 120.3, 119.0, 111.1, 110.3.

Compound 14 was diluted in CHCl$_3$ to a concentration of 0.2 mM and a UV Spectrum of the diluted Compound 14 was obtained. Maximum absorption wavelength was 329 nm.

Td and Tg of Compound 14 were measured by performing thermal analysis using TGA and DSC under the following conditions: N$_2$ atmosphere, temperatures of room temperature to 600° C. (10° C./min)-TGA and of room temperature to 400° C.-DSC, and Pan Type: Pt Pan in disposable Al Pan (TGA) and disposable Al pan (DSC). The measured Td was 533° C. and Tg was 174° C.

A HOMO level of 5.2 eV and a LUMO level of 2.27 eV were obtained using AC-2 that measures UV absorption spectrum and ionization potential.

Synthesis Example 6

Synthesis Compound 28

Compound 28 was synthesized through Reaction Scheme 7 below.

Intermediate H was synthesized with a yield of 80% in the same manner as in Synthesis Example 1, except that 3,6-dibromocarbozole was used instead of carbazole in the synthesis of Intermediate A of Synthesis Example 1. Then, Intermediate I was synthesized with a yield of 85% in the same manner as in Synthesis Example 1, except that Intermediate H was used instead of 4,4'-dibromodiphenyl in the synthesis of Intermediate C of Synthesis Example 1. Then, 2.3 g (Yield 81%) of Compound 28 as a yellow solid powder was produced in the same manner as in Synthesis Example 1, except that Intermediates B and I were used instead of Intermediates B and C in the synthesis of Compound 8 of Synthesis Example 1.

$^{1}$H NMR(C$_6$D$_6$, 300 MHz) δ (ppm) 8.13 (s, 2H), 8.04 (s, 2H), 7.65 (d, 2H), 7.39-7.31 (m, 4H), 7.27-7.22 (m, 12H), 7.19-6.99 (m, 21H), 6.82 (t, 2H); $^{13}$C NMR (C$_6$D$_6$, 100 MHz) δ (ppm) 150.4, 142.1, 141.9, 141.8, 138.8, 138.2, 138.0, 130.0, 129.9, 129.4, 128.3, 128.0, 127.8, 127.7, 127.3, 127.2, 127.1, 126.4, 126.3, 125.2, 125.1, 125.0, 123.8, 121.0, 120.7, 120.4, 120.2, 119.0, 117.7, 111.2, 110.9, 109.9.

Compound 28 was diluted in CHCl$_3$ to a concentration of 0.2 mM and UV Spectrum of the diluted Compound 28 was obtained. Maximum absorption wavelengths were 315 and 248 nm.

Td and Tg of Compound 28 were measured by performing thermal analysis using TGA and DSC under the following conditions: N$_2$ atmosphere, temperatures of room temperature to 600° C. (10° C./min)-TGA and of room temperature to 400° C.-DSC, and Pan Type: Pt Pan in disposable Al Pan (TGA) and disposable Al pan (DSC). The measured Td was 460° C. and Tg was 175° C.

A HOMO level of 5.0 eV and a LUMO level of 2.09 eV were obtained using AC-2 that measures UV absorption spectrum and ionization potential.

Synthesis Example 7

Synthesis Compound 35

Compound 35 was synthesized through Reaction Scheme 8 below.

Reaction Scheme 8

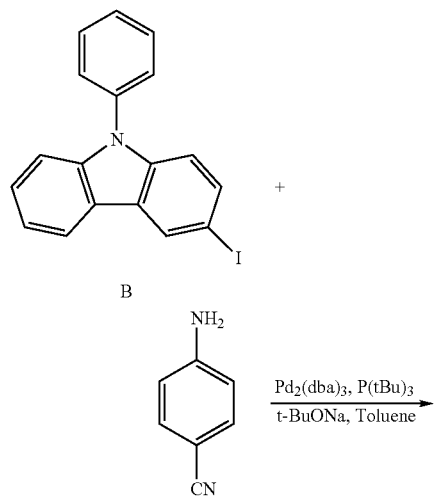

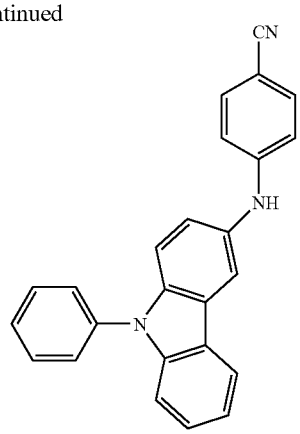

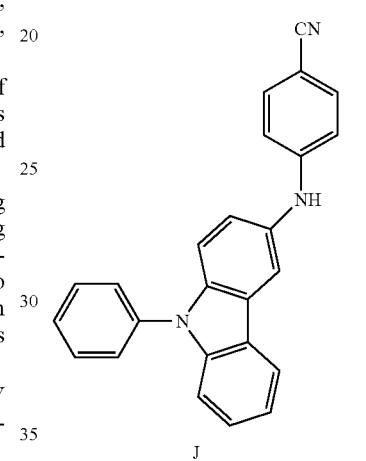

J

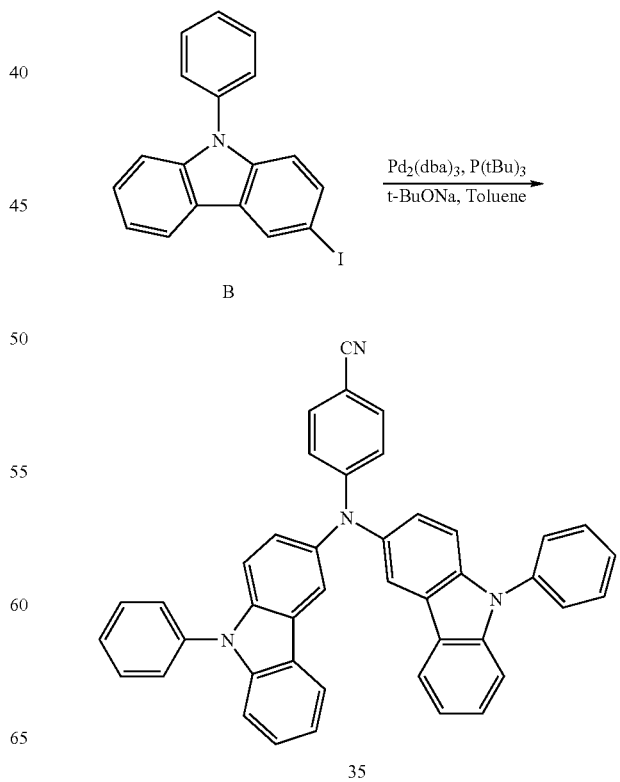

35

Synthesis of Intermediate J 0.316 g (0.856 mmol) of Intermediate B, 0.142 g (1.2 mmol) of 4-aminobenzonitril were dissolved in 5 ml of toluene and 0.144 g (1.5 mmol) of t-BuONa, 0.018 g (0.02 mmol) of Pd(dba)$_2$, and 0.004 to 0.006 g (0.02 to 0.03 mmol) of (t-Bu)$_3$P were added thereto. The mixture was stirred at 80° C. for 5 hours. The resultant solution was extracted three times with 20 ml of ethylether. An organic layer collected from the mixture was dried over MgSO$_4$ to evaporate the solvent. As a result, the dried result was purified using a silica gel column chromatography to produce 0.218 g of Intermediate J (Yield 71%).

Synthesis of Compound 35

0.221 g (0.614 mmol) of Intermediate J, 0.332 g (0.9 mmol) of Intermediate B were dissolved in 10 ml of toluene and 0.144 g (1.5 mmol) of t-BuONa, 0.018 g (0.02 mmol) of Pd(dba)$_2$ and 0.004 to 0.006 g (0.02 to 0.03 mmol) of (t-Bu)$_3$P were added thereto. The mixture was stirred at 90° C. for 6 hours. The resultant solution was extracted three times with 30 ml of ethylether. An organic layer collected from the mixture was dried over MgSO$_4$ to evaporate the solvent. As a result, the dried result was purified using a silica gel column chromatography to produce 0.236 g of Compound 35 (Yield 64%). Compound 35 was identified by $^1$H-NMR.

$^1$H-NMR (CDCl$_3$, 400 MHz) δ (ppm) 8.05 (d, 2H), 8.03 (dd,2H), 7.58 (m, 8H), 7.47 (m, 2H), 7.39 (m, 8H), 7.33 (dd, 2H), 7.24 (m, 2H), 6.94 (d, 2H).

Synthesis Example 8

Synthesis Compound 56

Compound 56 was synthesized through Reaction Scheme 9 below.

Reaction Scheme 9

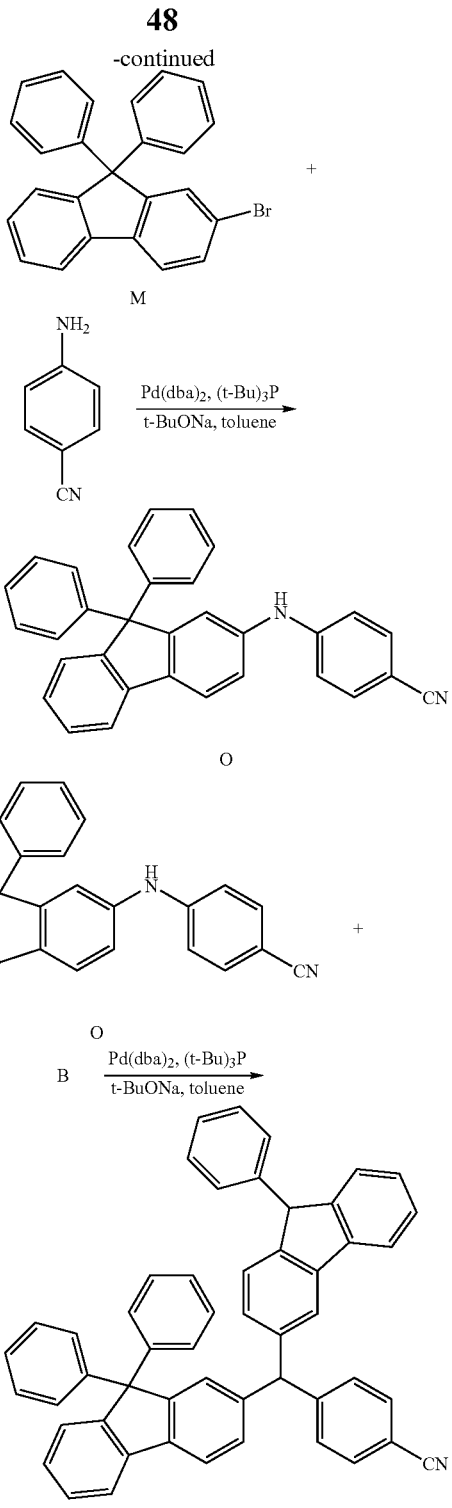

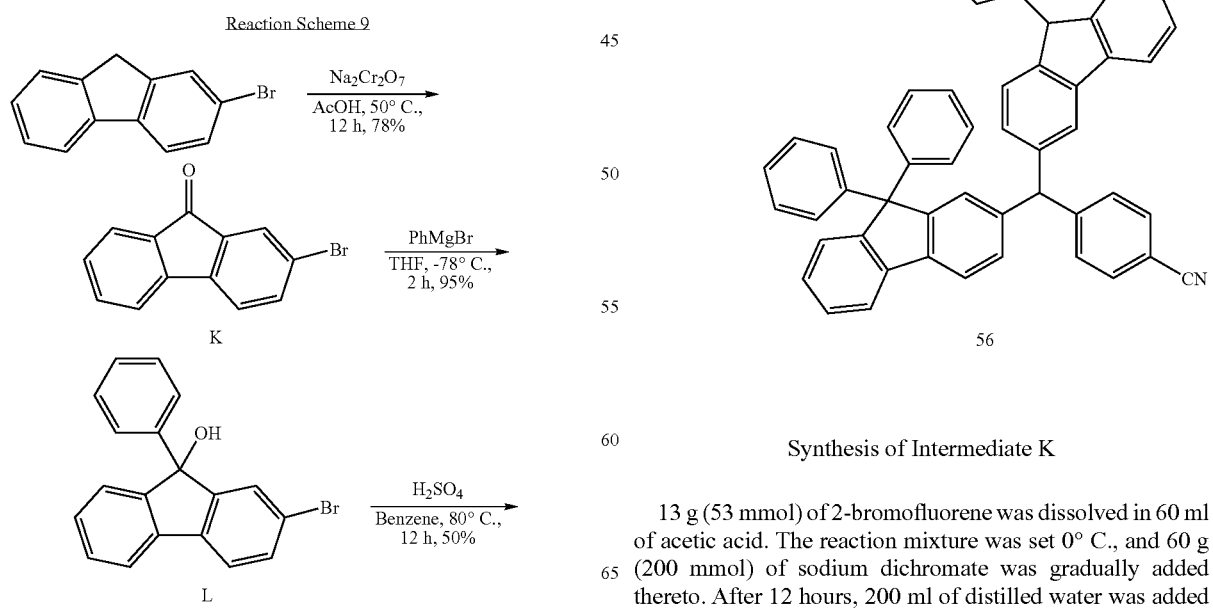

Synthesis of Intermediate K 13 g (53 mmol) of 2-bromofluorene was dissolved in 60 ml of acetic acid. The reaction mixture was set 0° C., and 60 g (200 mmol) of sodium dichromate was gradually added thereto. After 12 hours, 200 ml of distilled water was added thereto and the reaction mixture was sufficiently stirred. The produced yellow solid was filtered and dried to produce 10 g of Intermediate K (Yield 78%).

Synthesis of Intermediate L 8 g (31.6 mmol) of Intermediate K was dissolved in 60 ml of THF. The temperature of the reaction mixture was set to −78° C., and 38 ml (38 mmol) of 1 M phenylmagnesium bromide was gradually added thereto. After 2 hours, the temperature was set to room temperature and stirred for 5 hours. The reaction mixture was diluted in 50 ml of ammonium chloride solution and extracted three times with 40 ml of ethylacetate. An organic layer collected from the mixture was dried over $MgSO_4$ to evaporate the solvent. As a result, the dried result was purified using a silica gel column chromatography to produce 10 g of Intermediate L (Yield 95%). Intermediate L was identified by $^1$H-NMR $^1$H NMR ($CDCl_3$, 400 MHz) δ (ppm) 7.64 (d, 1H), 7.54-7.47 (m, 2H), 7.44 (d, 1H), 7.39-7.33 (m, 3H), 7.30-7.23 (m, 5H), 2.46 (s, 1H)

Synthesis of Intermediate M 10 g (30 mmol) of Intermediate L was dissolved in 60 ml of benzene. 2.4 ml (45 mmol) of sulfuric acid diluted in a small amount of benzene was added thereto. The reaction mixture was stirred at 80° C. for 5 hours. After the benzene was evaporated, 1 N NaOH was added to the reaction solution to adjust the pH of the reaction solution to 7. Then, the resultant solution was extracted three times with 40 ml of ethylacetate. An organic layer collected from the mixture was dried over $MgSO_4$ to evaporate the solvent. As a result, the dried result was purified using a silica gel column chromatography to produce 6 g of Intermediate M (Yield 50%).

Synthesis of Intermediate O 340 mg (0.856 mmol) of Intermediate M, 142 mg (1.2 mmol) of 4-aminobenzonitril were dissolved in 5 ml of toluene and 0.144 g (1.5 mmol) of t-BuONa, 0.018 g (0.02 mmol) of Pd(dba)$_2$, and 0.004 to 0.006 g (0.02 to 0.03 mmol) of (t-Bu)$_3$P were added thereto. The mixture was stirred at 80° C. for 5 hours. The resultant solution was extracted three times with 20 ml of ethylether. An organic layer collected from the mixture was dried over $MgSO_4$ to evaporate the solvent. As a result, the dried result was purified using a silica gel column chromatography to produce 0.27 g of Intermediate O (Yield 73%).

Synthesis of Compound 56

267 mg (0.614 mmol) of Intermediate O, 0.332 g (0.9 mmol) of Intermediate B (refer to Synthesis Example 1) were dissolved in 10 ml of toluene and 0.144 g (1.5 mmol) of t-BuONa, 0.018 g (0.02 mmol) of Pd(dba)$_2$, and 0.004 to 0.006 g (0.02 to 0.03 mmol) of (t-Bu)$_3$P were added thereto. The mixture was stirred at 90° C. for 6 hours. The resultant solution was extracted three times with 30 ml of ethylether. An organic layer collected from the mixture was dried over $MgSO_4$ to evaporate the solvent. As a result, the dried result was purified using a silica gel column chromatography to produce 0.236 g of Compound 56 (Yield 57%). Compound 56 was identified by $^1$H-NMR.

$^1$H NMR ($CDCl_3$, 400 MHz) δ (ppm) 7.97 (d, 1H), 7.90 (d,1H), 7.69 (d, 1H), 7.65 (d, 1H), 7.60 (d, 2H), 7.56 (dd, 2H), 7.48 (m, 1H), 7.40 (d, 2H), 7.35 (m, 6H), 7.24 (m, 3H), 7.16 (m, 10H), 7.11 (dd, 1H), 6.93 (d, 2H)

Example 1

An aluminium and ITO glass (SDI Co., Ltd.) substrate (1,300 Å) was cut into pieces of 50 mm×50 mm×0.7 mm in size, followed by ultrasonic cleaning in isopropyl alcohol and deionized water (5 minutes for each) and then UV/ozone cleaned (30 minutes) to produce a reflective electrode.

Then, Compound 8 was deposited on the reflective electrode to form a HIL with a thickness of 1,200 Å, and NPB was deposited on the HIL to form a HTL with a thickness of 300 Å.

IDE 140 (Idemitsu Corporation) as a blue fluorescent host and IDE 105 (Idemitsu Corporation) as a blue fluorescent dopant were deposited at the same time in a weight ratio of 98:2 on the HTL to form a blue EML with a thickness of 300 Å. Then, Balq was deposited on the blue EML to form a HBL with a thickness of 50 Å. Alq3 was deposited on the HBL to form an ETL with a thickness of 250 Å. LiF was deposited on the ETL to form an EIL with a thickness of 3 Å, and then Mg:Ag was deposited on the EIL to form a semitransparent electrode with a thickness of 180 Å. As a result, an organic light emitting device was manufactured.

At a driving voltage of 5.5 V, the current density of the organic light emitting device was 23.0 mA/cm$^2$, the luminance was 1,179 cd/m$^2$, the color coordinates were (0.113, 0.130), and the light emitting efficiency was 5.13 cd/A.

Example 2

An organic light emitting device was manufactured in the same manner as in Example 1 except that Compound 9 was used instead of Compound 8 in the formation of a HIL.

At a driving voltage of 5.5 V, the current density of the organic light emitting device was 20.1 mA/cm$^2$, the luminance was 1,021 cd/m$^2$, the color coordinates were (0.113, 0.120), and the light emitting efficiency was 5.10 cd/A.

Example 3

An organic light emitting device was manufactured in the same manner as in Example 1 except that IDE 406 (Idemitsu Corporation) was used instead of Compound 8 in the formation of a HIL.

At a driving voltage of 5.5 V, the current density of the organic light emitting device was 46.52 mA/cm$^2$, the luminance was 784 cd/m$^2$, the color coordinates were (0.113, 0.125), and the light emitting efficiency was 4.74 cd/A.

Example 4

An organic light emitting device was manufactured in the same manner as in Example 1 except that Li273 (Sensient, Germany) was used instead of Compound 8 in the formation of a HIL.

At a driving voltage of 5.5 V, the current density of the organic light emitting device was 17.43 mA/cm$^2$, the luminance was 695 cd/m$^2$, the color coordinates were (0.122, 0.110), and the light emitting efficiency was 3.98 cd/A.

Example 5

An organic light emitting device was manufactured in the same manner as in Example 1 except that HI102 (UDC, U.S.A.) was used instead of Compound 8 in the formation of a HIL.

At a driving voltage of 5.5 V, the current density of the organic light emitting device was 0.67 mA/cm$^2$, the luminance was 1.2 cd/m$^2$, the color coordinates were (0.112, 0.154), and the light emitting efficiency was 0.18 cd/A.

Example 6

An organic light emitting device was manufactured in the same manner as in Example 1 except that ELM180 (ELM, Korea) was used instead of Compound 8 in the formation of a HIL.

At a driving voltage of 5.5 V, the current density of the organic light emitting device was 2.55 mA/cm$^2$, the brightness was 52 cd/m$^2$, the color coordinates were (0.124, 0.105), and the light emitting efficiency was 2.04 cd/A.

Figure 3:
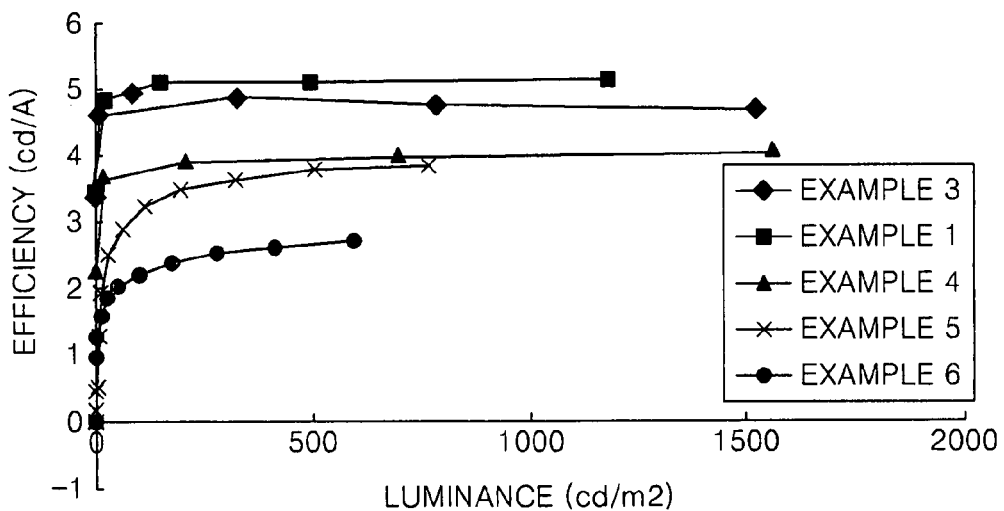
FIGS. 3 through 7 are graphs illustrating current efficiencies, luminance, and driving voltages of an organic light emitting device according to an embodiment of the present invention.

Referring to Examples 1 through 6, when Compound 8 or 9 was used to form the HIL or the thickness of the HIL was controlled according to an embodiment of the present invention, the hole injecting capability increased, and thus the current densities and the current efficiencies of the organic light emitting devices increased at the same driving voltage and luminance increased. The results of the current efficiencies at the same voltage are illustrated in FIG. 3.

Figure 4:
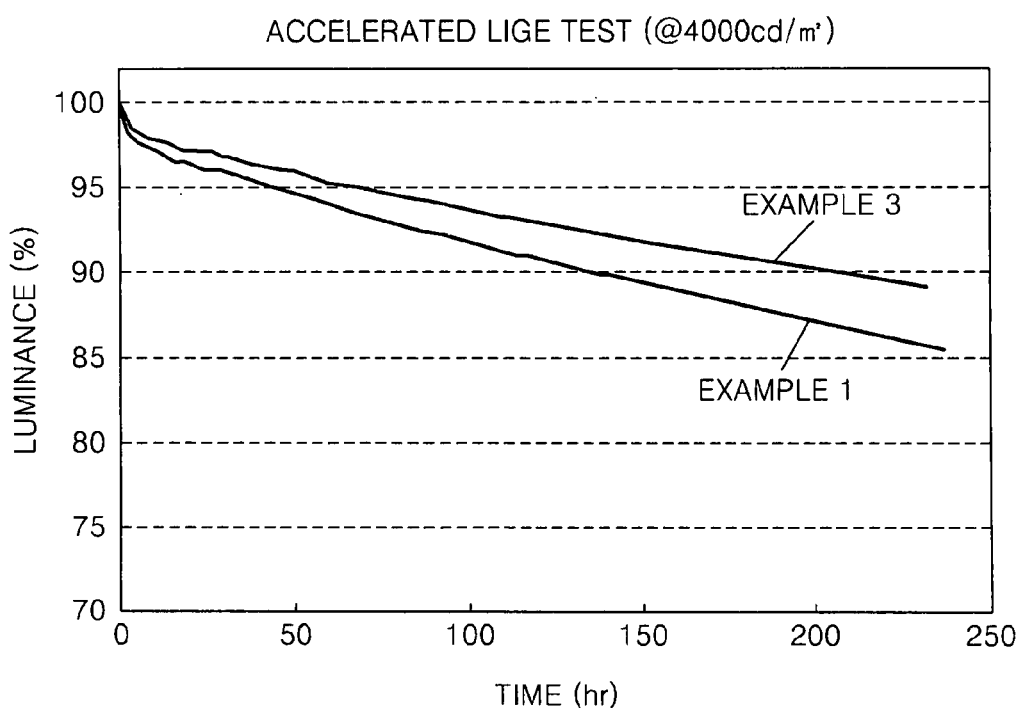
Figure 5:
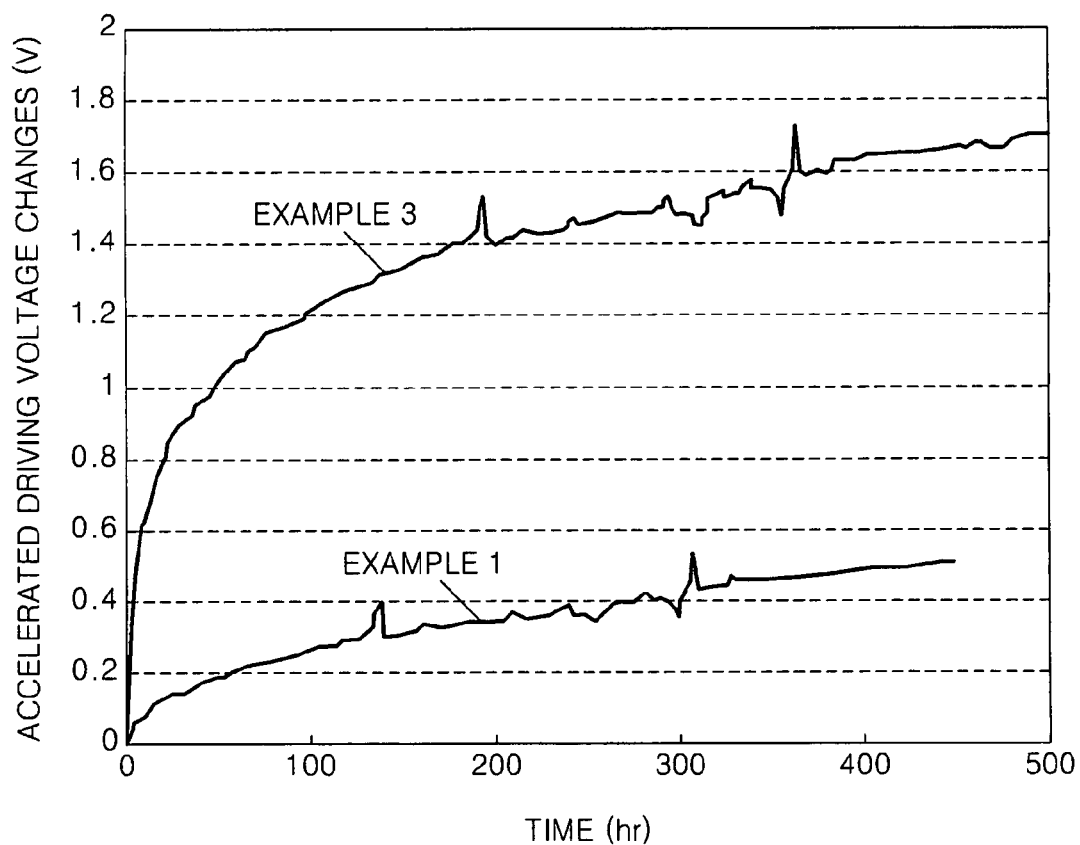

The evaluation results for the luminance changes and driving voltage changes of the organic light emitting devices according to Examples 1 and 3 are shown in FIGS. 4 and 5. An accelerated life test was performed to measure luminance changes of the organic light emitting devices of Examples 1 and 3. The luminances were measure after 200 hours at 4,000 cd/m$^2$ as shown in FIG. 4. The luminance of the organic light emitting device of Example 1 after 200 hours at 4,000 cd/m$^2$ was 90.2% of the initial luminance, and the luminance of the organic light emitting device of Example 3 after 200 hours at 4,000 cd/m$^2$ was 86.2% of the initial luminance. FIG. 5 illustrates the accelerated life test results of the driving voltage changes after 400 hours at 4,000 cd/m$^2$. The driving voltage of the organic light emitting device of Example 1 increased by 0.45 V and the driving voltage of the organic light emitting device of Example 3 increased by 1.65 V. Referring to FIG. 5, the organic light emitting device of Example 1 has low power consumption and low driving voltage.

Example 7

An organic light emitting device was manufactured in the same manner as in Example 1 except that Compound 11 was deposited on the electrode to form a HIL with a thickness of 1600 Å, and CBP and Ir(ppy)$_3$ as green light emitting materials were deposited on the HTL to form a green EML with a thickness of 300 Å instead of the blue EML.

At a driving voltage of 5 V, the current density of the organic light emitting device was 7.5 mA/cm$^2$, the luminance was 2220 cd/m$^2$, the color coordinates were (0.244, 0.71), and the light emitting efficiency was 29.6 cd/A.

Example 8

An organic light emitting device was manufactured in the same manner as in Example 7 except that IDE 406 (Idemitsu Corporation) was used instead of Compound 11 in the formation of a HIL.

At a driving voltage of 5 V, the current density of the organic light emitting device was 7.86 mA/cm$^2$, the luminance was 1,900 cd/m$^2$, the color coordinates were (0.246, 0.691), and the light emitting efficiency was 23.9 cd/A.

Figure 6:
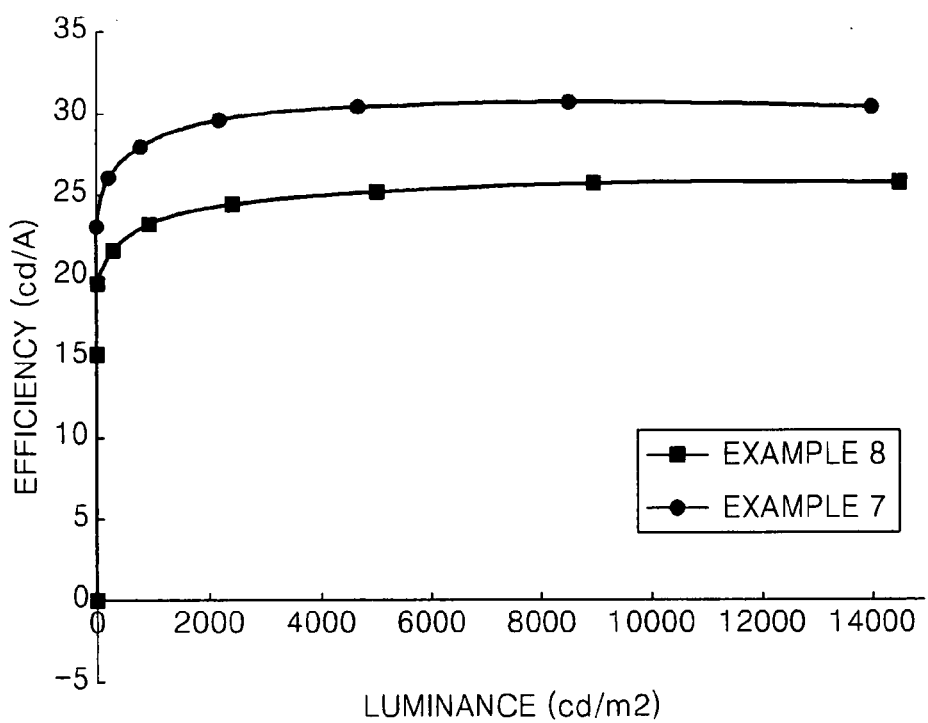

The current efficiencies of Examples 7 and 8 are shown in FIG. 6.

Example 9

An organic light emitting device was manufactured in the same manner as in Example 1 except that Compound 14 was deposited on the electrode to form a HIL with a thickness of 2000 Å, and CBP and BPTIr as red light emitting materials were deposited on the HTL to form a red EML with a thickness of 300 Å instead of the blue EML.

At a driving voltage of 5 V, the current density of the organic light emitting device was 11.8 mA/cm$^2$, the luminance was 1,534 cd/m$^2$, the color coordinates were (0.687, 0.310), and the light emitting efficiency was 13.0 cd/A.

Example 10

An organic light emitting device was manufactured in the same manner as in Example 9 except that IDE 406 (Idemitsu Corporation) was used instead of Compound 14 in the formation of a HIL.

At a driving voltage of 5 V, the current density of the organic light emitting device was 13.3 mA/cm$^2$, the brightness was 1328 cd/m$^2$, the color coordinates were (0.692, 0.306), and the light emitting efficiency was 9.98 cd/A.

Figure 7:
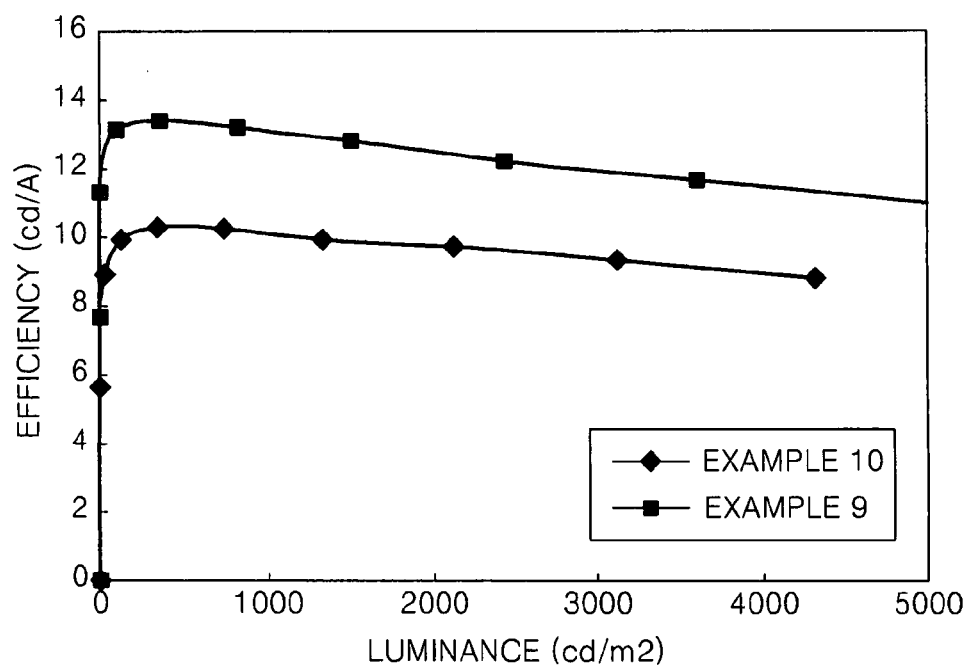

The current efficiencies of Examples 9 and 10 are shown in FIG. 7.

The driving voltage, efficiency, and color purity characteristics of the organic light emitting devices of Examples 1-10 were evaluated using an IVL measuring device (PhotoResearch PR650, Keithley 238).

Example 11

An organic light emitting device including red, s green, and blue EMLs was manufactured as follows.

A substrate having a thin film transistor was prepared, and a first electrode composed of Al was formed in a stripe shape with a thickness of 1000 Å. Here, the first electrode was electrically connected to a source electrode or a drain electrode of the thin film transistor formed on the substrate.

Red, green and blue sub-pixel defining layers which define regions in which the red, green, and blue EMLs will be formed were formed on the first electrode using a silicon oxide. Compound 8 was deposited on the regions in which the red, green and blue EML will be formed to form a HIL. Compound 8 was deposited on the region in which the red EML will be formed to a thickness of 2000 Å, on the region in which the green EML will be formed a thickness of 1600 Å, and on the region in which the blue EML will be formed to a thickness of 1200 Å to form the HIL. Then, NPB was deposited on the HIL to form a HTL with a thickness of 300 Å.

CBP and BPTIr as red light emitting materials were deposited on the HTL to form a red EML with a thickness of 300 Å, CBP and Irppy as green light emitting materials were deposited on the HTL to form a green EML with a thickness of 300 Å, and IDE 140 (Idemitsu Corporation) and IDE 105 (Idemitsu Corporation) as blue light emitting materials were deposited on the HTL to form a blue EML with a thickness of 150 Å.

Then, Balq was deposited on the red, green and blue EMLs to form a HBL 11 with a thickness of 50 Å. Alq3 was deposited on the HBL to form an ETL with a thickness of 250 Å. LiF was deposited on the ETL to form an EIL with a thickness of 3 Å, and then Mg:Ag was deposited on the EIL to form a semitransparent electrode with a thickness of 180 Å. As a result, an organic light emitting device including the red, green, and blue EMLs was manufactured.

The efficiency and the color coordinates of the organic light emitting device of Example 11 were measured in the same manner as in Examples 1 through 10. The results are shown in Table 1.

TABLE 1

|  | Efficiency (cd/A) | x Color Coordinate | y Color Coordinate |
|---|---|---|---|
| Red EML | 13.4 | 0.68 | 0.32 |
| Green EML | 29.9 | 0.22 | 0.73 |
| Blue EML | 2.9 | 0.14 | 0.06 |

As shown in Table 1, each EML of the organic light emitting device of Example 11 exhibited excellent efficiency and color purity. The efficiency of white light comprising a mixture of red, green, and blue light in the organic light emitting device of Example 11 was 13.0 cd/A at a luminance of 150 cd/m$^2$ when 40% of the device was operating, and power consumption was 180 mW. The efficiency and color purity characteristics of the organic light emitting device of Example 11 were evaluated using an IVL measuring device (PhotoResearch PR650, Keithley 238) and the power consumption was calculated.

Example 12

An organic light emitting device was manufactured in the same manner as in Example 11 except that IDE 406 (Idemitsu Corporation) was used instead of Compound 8 to form a HIL. The efficiency and the color coordinates of the organic light emitting device of Example 12 are shown in Table 2.

TABLE 2

|  | Efficiency (cd/A) | x Color Coordinate | y Color Coordinate |
|---|---|---|---|
| Red EML | 12.1 | 0.67 | 0.32 |
| Green EML | 25.4 | 0.23 | 0.73 |
| Blue EML | 2.24 | 0.14 | 0.06 |

As shown in Table 2, each EML of the organic light emitting device of Example 12 exhibited excellent efficiency and color purity. The efficiency of white light comprising a mixture of red, green, and blue light in the organic light emitting device of Example 12 was 11.0 cd/A at a brightness of 150 cd/m$^2$ when 40% of the device was operating, and power consumption was 220 mW. The efficiency and color purity characteristics of the organic light emitting device of Example 12 were evaluated using an IVL measuring device (PhotoResearch PR650, Keithley 238) and the power consumption was calculated.

Comparative Example 1

A substrate having a thin film transistor was prepared, and a first electrode composed of Al was formed in a stripe shape with a thickness of 1000 Å. Here, the first electrode was electrically connected to a source electrode or a drain electrode of the thin film transistor formed on a lower portion of the substrate.

Red, green and blue pixel defining layers which define regions in which red, green, and blue emission layers will be formed were formed on the pixel electrode using a silicon oxide. M-TDATA was deposited on the regions in which red, green and blue emission layers will be formed form a HIL with a thickness of 1000 Å. Then NPB was deposited on the HIL to form a HTL with a thickness of 400 Å. In addition, NPB was further deposited over the region in which green EML will be formed to a thickness of 400 Å using a photomask. NPB was further deposited over the region in which red EML will be formed to a thickness of 800 Å. As a result, HTL having total thickness of 1200 Å in the region in which red EML will be formed, total thickness of 800 Å in the region in which green EML will be formed an to total thickness of 400 Å in the region in which blue EML will be formed.

CBP and BPTIr as red light emitting materials were deposited on the red HTL to form a red EML with a thickness of 300 Å, CBP and Irppy as green light emitting materials were deposited on the green HTL to form a green EML with a thickness of 300 Å, and IDE 140 (Idemitsu Corporation) and IDE 105 (Idemitsu Corporation) as blue light emitting materials were deposited on the blue HTL to form a blue EML with a thickness of 150 Å.

Then, Balq was deposited on the red, green and blue EMLs to form a HBL with a thickness of 50 Å. Alq3 was deposited on the HBL to form an ETL with a thickness of 250 Å. LiF was deposited on the ETL to form an EIL with a thickness 9 of 3 Å, and then Mg:Ag was deposited on the EIL to form a semitransparent electrode with a thickness of 180 Å. As a result, an organic light emitting device including the red, green, and blue EMLs was manufactured.

The efficiency and the color coordinates of the organic light emitting device of Comparative Example 1 are shown in Table 3.

TABLE 3

|  | Efficiency (cd/A) | x Color Coordinate | y Color Coordinate |
|---|---|---|---|
| Red EML | 5.39 | 0.67 | 0.32 |
| Green EML | 24.45 | 0.21 | 0.72 |
| Blue EML | 1.40 | 0.14 | 0.06 |

As shown in Table 3, the organic light emitting device of Example 11 having a material used to form a HIL according to an embodiment of the present invention and the organic light emitting device of Example 12 having the thickness of the HIL according to an embodiment of the present invention exhibited greater efficiency and color purity than the organic light emitting device of Comparative Example 1.

An organic light emitting device according to the present invention includes an organic layer containing one of the compounds represented by Formulae 1, 2, and 3 between a pair of electrodes capable of generating resonance during the operation of the device; and/or a hole injection layer having the thickness range described above between the pair of electrodes. The organic light emitting device of the present invention has low driving voltage, excellent current density, high brightness, excellent color purity, high efficiency, and long lifetime. In particular, the organic light emitting device of the present invention has excellent lifetime property. A flat panel display device having enhanced reliability can be obtained by employing the organic light emitting device of the present invention.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A compound represented by the following Formula:

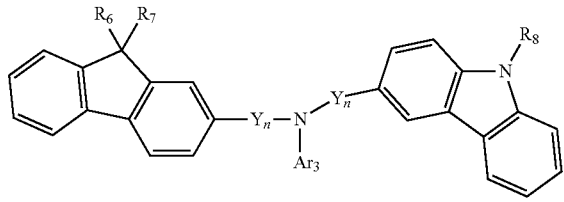

where $R_6$, $R_7$ and $R_8$ are each independently one selected from a group consisting of a hydrogen atom, a substituted or unsubstituted $C_1$-$C_{30}$ alkyl group, a substituted or unsubstituted $C_1$-$C_{30}$ alkoxy group, a substituted or unsubstituted $C_6$-$C_{30}$ aryl group, a substituted or unsubstituted $C_6$-$C_{30}$ aryloxy group, a substituted or unsubstituted $C_4$-$C_{30}$ hetero ring, a substituted or unsubstituted $C_5$-$C_{30}$ polycyclic condensed ring, a hydroxy group, a cyano group, and a substituted or unsubstituted amino group, wherein two or more of $R_6$ $R_7$ and $R_8$ can be optionally bound with one another to form a saturated or unsaturated carbon ring;

$Ar_3$ is a biphenyl group;

each Y is independently one selected from the group consisting of a substituted or unsubstituted $C_1$-$C_{30}$ alkyl group, a substituted or unsubstituted $C_6$-$C_{30}$ aryl group, and a substituted or unsubstituted $C_4$-$C_{30}$ hetero ring; and wherein n of the $Y_n$ between the carbazole and the nitrogen is 1, and n of the $Y_n$ between the fluorene and the nitrogen is 0.

2. A compound of claim 1, wherein $R_6$ and $R_7$ are each a methyl group and $R_8$ is a phenyl.

3. The compound of claim 1 with the following chemical structure:

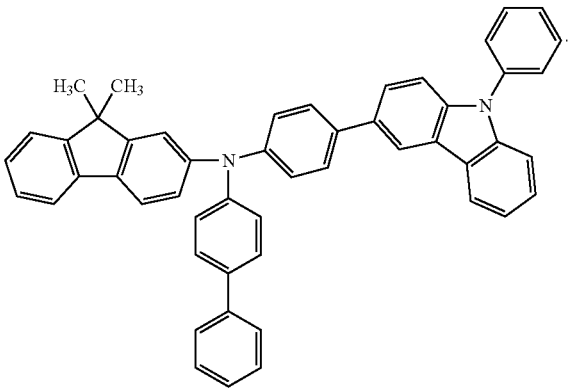

* * * * *